US011241209B2

(12) United States Patent
Shinden et al.

(10) Patent No.: US 11,241,209 B2
(45) Date of Patent: Feb. 8, 2022

(54) DEVICE AND SYSTEM FOR DETERMINING A BONE STRENGTH INDICATOR

(71) Applicant: Konica Minolta, Inc., Tokyo (JP)

(72) Inventors: Yuko Shinden, Hino (JP); Yoshihide Hoshino, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 116 days.

(21) Appl. No.: 16/513,851

(22) Filed: Jul. 17, 2019

(65) Prior Publication Data

US 2020/0022665 A1 Jan. 23, 2020

(30) Foreign Application Priority Data

Jul. 20, 2018 (JP) .............................. JP2018-136288

(51) Int. Cl.
*A61B 6/00* (2006.01)
*G06T 7/00* (2017.01)
*G16H 30/40* (2018.01)
*A61B 5/00* (2006.01)
*G06T 11/00* (2006.01)

(52) U.S. Cl.
CPC ............ *A61B 6/505* (2013.01); *A61B 6/4291* (2013.01); *A61B 6/463* (2013.01); *A61B 6/5217* (2013.01); *G06T 7/0012* (2013.01); *A61B 5/4509* (2013.01); *A61B 6/483* (2013.01); *A61B 6/5235* (2013.01); *G06T 11/00* (2013.01); *G16H 30/40* (2018.01)

(58) Field of Classification Search
CPC ... G06K 2209/05; G06T 7/0012; G06T 7/521; G06T 2207/30004; G06T 11/00; G06T 2207/10116; G06T 2207/30008; G16H 30/40; G16H 50/30; A61B 6/505; A61B 6/4291; A61B 6/463; A61B 6/5217; A61B 5/4509; A61B 6/483; A61B 6/5235; A61B 5/004; A61B 5/4504; A61B 6/469; A61B 6/482; A61B 6/5205; A61B 6/5282; A61B 6/4035; A61B 6/484
See application file for complete search history.

(56) References Cited

U.S. PATENT DOCUMENTS

2010/0111395 A1\* 5/2010 Tamakoshi ............ G06T 7/0012
382/132
2015/0131777 A1\* 5/2015 Makifuchi ............. A61B 6/463
378/36

FOREIGN PATENT DOCUMENTS

JP          6197790         9/2017
WO    WO 2009/110260 A1    9/2009

OTHER PUBLICATIONS

European Patent Application No. 19180509.2; Partial Search Report; dated Nov. 27, 2019; 13 pages.
Eggl et al., Prediction of Vertebral Failure Load by Using X-Ray Vector Radiographic Imaging, Radiology, vol. 275(2), pp. 553-561 (May 2015).

\* cited by examiner

*Primary Examiner* — Siamak Harandi
(74) *Attorney, Agent, or Firm* — BakerHostetler

(57) ABSTRACT

Disclosed is a way to provide a medical image processing device that may include a hardware processor that calculates at least one of trabecular connectivity, trabecular width, trabecular number, mineralization degree, osteoid volume, cortical width, and cortical porosity as a bone characteristic indicator of a subject from reconstructed image data generated from moiré image data acquired by photographing the subject.

19 Claims, 16 Drawing Sheets

DEVICE AND SYSTEM FOR DETERMINING A BONE STRENGTH INDICATOR

CROSS REFERENCE TO RELATED APPLICATIONS

This application claims priority to Japanese Patent Application No. 2018-136288, filed on Jul. 20, 2018, which is incorporated herein by reference in its entirety.

BACKGROUND

Technological Field

The present disclosure relates to a medical image processing device and a medical image photographing system.

Description of the Related Art

As an X-ray photographing device, conventionally known is an X-ray photographing device (referred to as an X-ray Talbot photographing device hereinafter) using a Talbot interferometer or a Talbot-Lau interferometer having one-dimensional grating. Further, through reconstructing moiré images (moiré fringe images) photographed by the X-ray Talbot photographing device, it is possible to acquire at least three kinds of high-definition reconstructed images such as an absorption image, a differential phase image, and a small-angle scattering image.

Further, also known is a medical image system that generates composite images of three kinds of reconstructed images acquired by a fringe scanning system and provides the composite images as diagnosis images (see Japanese Patent No. 6197790).

Furthermore, also known is a method for measuring cancellous bone trabecular anisotropy by using Talbot small-angle scattering images of a same body part with different set angle positions with respect to the grating (see Non-Patent Literature (Elena Eggl et al (2015), Prediction of Vertebral Failure Load by Using X-Ray Vector Radiographic Imaging, Radiology: Vol. 275: Number 2: p 553-561)).

Highly accurate bone strength evaluation is necessary for reducing a risk of having fractures due to osteoporosis, and the bone strength is determined by "bone density+bone factors". The bone density measured by an existing method such as DEXA (Dual-Energy X-ray Absorptiometry) is not sufficiently correlated with the bone strength, and it is widely known that measurement of material/structure factors (=bone factors) other than the bone density is necessary for grasping the accurate bone strength. However, it is not possible with conventional bone factor measurement methods to easily acquire the bone factors other than the trabecular anisotropy depicted in Non-Patent Literature mentioned above.

SUMMARY

It is an object of the present disclosure to easily acquire the bone factors other than the trabecular anisotropy.

To achieve at least one of the abovementioned objects, according to an aspect of the present disclosure, a medical image processing device reflecting one aspect of the present disclosure may include a hardware processor that calculates at least one of trabecular connectivity, trabecular width, trabecular number, mineralization degree, osteoid volume, cortical width, and cortical porosity as a bone characteristic indicator of a subject from reconstructed image data generated from moiré image data acquired by photographing the subject.

BRIEF DESCRIPTION OF THE DRAWINGS

The advantages and features provided by one or more embodiments of the disclosure will become more fully understood from the detailed description given hereinbelow and the appended drawings, which are given by way of illustration only and thus are not intended as a definition of the limits of the present disclosure.

DETAILED DESCRIPTION OF EMBODIMENTS

Hereinafter, one or more embodiments of the present disclosure will be described with reference to the drawings. However, the scope of the disclosure is not limited to the disclosed embodiments. The embodiments according to the present disclosure will be described with reference to the accompanying drawings.

Figure 1:
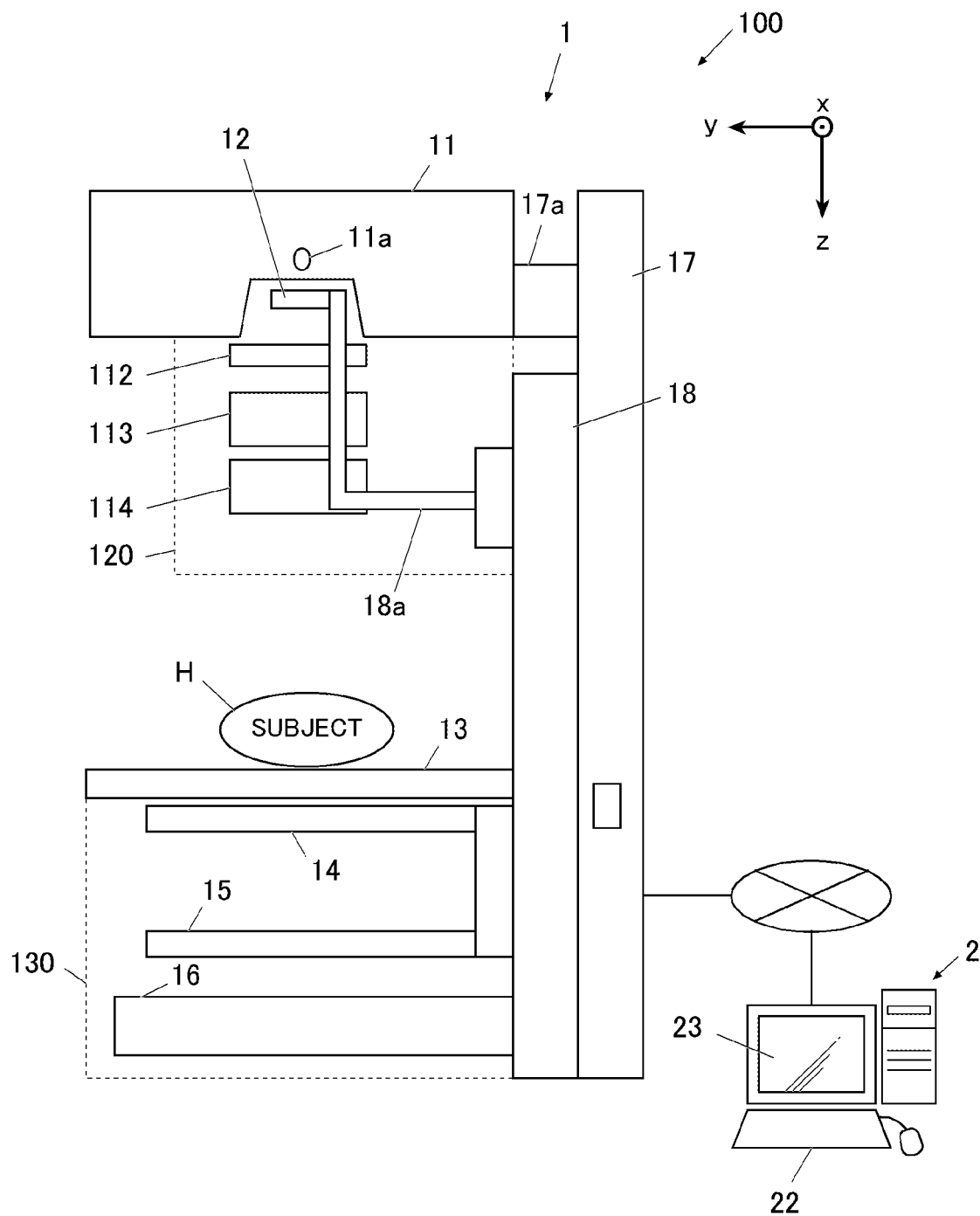
FIG. 1 is a schematic diagram illustrating an X-ray photographing system according to an embodiment of the present disclosure.

First, a device configuration according to the embodiment will be described with reference to FIG. 1 to FIG. 4. FIG. 1 is a schematic diagram illustrating an X-ray photographing system 100 according to the embodiment.

As illustrated in FIG. 1, in the embodiment, the X-ray photographing system 100 as a medical image photographing system is used. The X-ray photographing system 100 includes an X-ray Talbot photographing device 1 as a medical image photographing device, and an image processing device 2 as a medical image processing device. A same body part of a subject H is photographed for a plurality of times by using the X-ray Talbot photographing device 1 while changing subject set angles, and a plurality of kinds of reconstructed image data are generated for each of the subject set angles by the image processing device 2 based on moiré image data read out by the X-ray Talbot photographing device 1.

As the X-ray Talbot photographing device 1, employed is a device using a Talbot-Lau interferometer that includes a source grating (also referred to as G0 grating) 12. Note that it is also possible to employ an X-ray Talbot photographing device using a Talbot interferometer that includes not the source grating 12 but a first grating (also referred to as a G1 grating) 14 and a second grating (also referred to as a G2 grating) 15.

The subject H of the embodiment is a body part such as the femur, vertebra, or the like where osteoporosis fracture tends to occur. However, the subject H is not limited to the femur or vertebra part but may be any body part of a human body or even may not be a human body. Further, while this method relates to the characteristic and strength of the bones, it may also be applied to evaluations of structures, material characteristics, and strength of structural components similar to the bones. For example, this method may be applied to evaluations of implants and fiber composite materials inserted into the body as a substitute for the bone.

About X-ray Talbot Photographing Device

As illustrated in FIG. 1, the X-ray Talbot photographing device 1 includes an X-ray generator 11, the source grating 12, a subject rest 13, the first grating 14, the second grating 15, an X-ray detector 16, a support 17, and a base 18.

With the X-ray Talbot photographing device 1, it is possible to reconstruct at least three kinds of images (referred to as reconstructed images) through photographing moiré images of the subject H at a prescribed position with respect to the subject rest 13 by a method based on the principle of the fringe scanning method and analyzing the moiré images by using a Fourier transform method. That is, the three kinds of images are: an absorption image (same as a normal X-ray absorption image) acquired by imaging an average component of the moiré fringe of the moiré image; a differential phase image acquired by imaging phase information of the moiré fringe; and a small-angle scattering image acquired by imaging visibility (clearness) of the moiré fringe. It is also possible to generate still more kinds of images by recomposing those three kinds of reconstructed images.

The fringe scanning method is a method for acquiring high-definition reconstructed images through performing reconstruction by using moiré images photographed M0 times while shifting 1/M0 of slit interval of one grating (M0 is a positive integer, absorption image is M0>2, and differential phase image and small-angle scattering image are M0>3) in a slit interval direction among a plurality of gratings.

Further, the Fourier transform method is a method that photographs one moiré image by the X-ray Talbot photographing device in a state where there is a subject and, in image processing, reconstructs and generates differential phase images and the like by performing Fourier transform or the like on the moiré image.

Figure 2A:
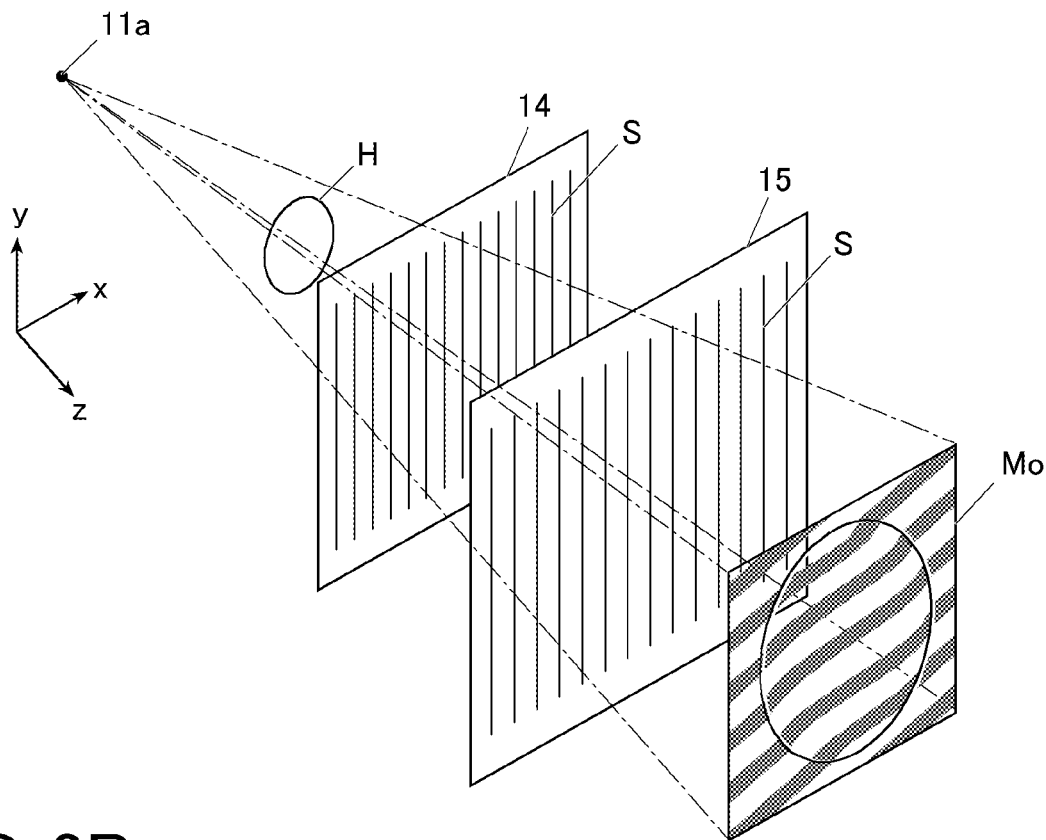
FIG. 2A is a view describing the principle of a Talbot interferometer.
Figure 2B:
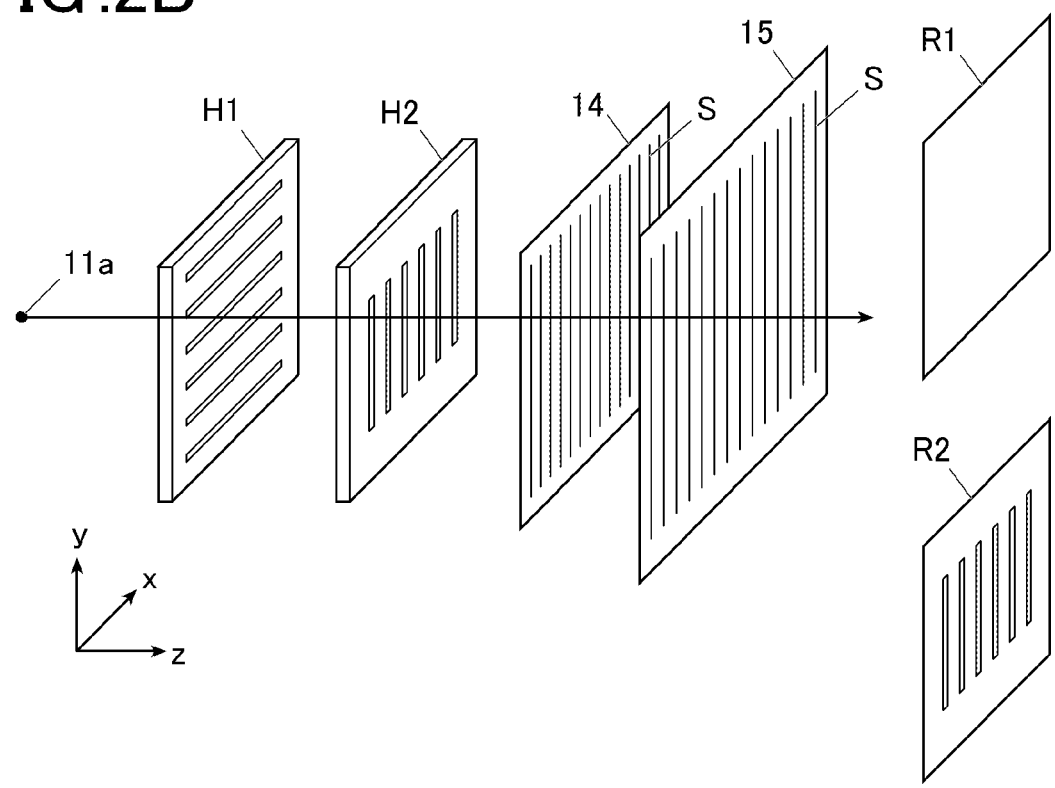
FIG. 2B is a view describing generation of a reconstructed image.
Figure 3:
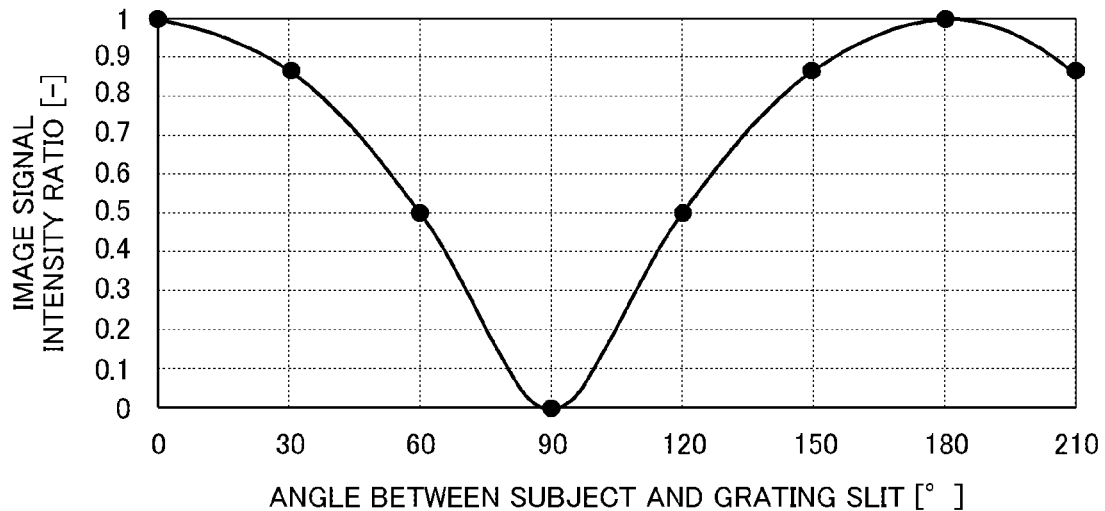
FIG. 3 is a graph illustrating image signal intensity ratios with respect to angles between a subject and a grating slit.

First, the principle common to the Talbot interferometer and the Talbot-Lau interferometer will be described by referring to FIG. 2A to FIG. 3. FIG. 2A is a view describing the principle of the Talbot interferometer. FIG. 2B is a view describing generation of reconstructed images R1 and R2. FIG. 3 is a graph illustrating image signal intensity ratios with respect to the angles between the subject and the grating slit.

While FIG. 2A illustrates the case of the Talbot interferometer, the case of the Talbot-Lau interferometer is also described basically in a similar manner. Further, z-direction in FIG. 2A corresponds to a vertical direction in the X-ray Talbot photographing device 1 of FIG. 1, and x-, y-directions in FIG. 2A correspond to horizontal directions (front and rear directions, left and right directions) in the X-ray Talbot photographing device 1 of FIG. 1.

Further, as illustrated in FIG. 2A, a plurality of slits S are formed sequentially at a prescribed interval in the first grating 14 and the second grating 15 (also in the source grating 12 in the case of the Talbot-Lau interferometer) in the x-direction orthogonal to the z-direction that is the irradiation direction of the X-ray.

As illustrated in FIG. 2A, when the X-ray irradiated from an X-ray source 11a (X-ray irradiated from the X-ray source 11a and shaped into multiple light sources by the source grating 12 in the case of the Talbot-Lau interferometer) transmits through the first grating 14, the transmitted X-ray forms an image at a specific interval in the z-direction. This image is referred to as a self image (also referred to as a grating image or the like), and a phenomenon where the self image is formed at a prescribed interval in the z-direction is called a Talbot effect.

That is, the Talbot effect means a phenomenon that forms the self image of coherent light at a prescribed interval in the traveling direction of the light as described above when the coherent light transmits through the first grating 14 where the slits S are provided at a prescribed interval.

Further, as illustrated in FIG. 2A, the second grating 15 where the slits S are provided in the same manner as in the case of the first grating 14 is placed at a position where the self image of the first grating 14 is formed. At that time, through placing the second grating 15 such that the extending direction of the slits thereof (that is, y-axis direction in FIG. 2A) comes to be substantially parallel to the extending direction of the slits S of the first grating 14, it is possible to acquire a moiré image Mo of interference fringes (moiré) on the second grating 15 generated by tilting the second grating 15 about the optical axis (axis connecting the X-ray focal point and the center of the grating) with respect to the first grating 14. In the case of photographing using the fringe scanning method, photographing can also be done through setting the relative angle between the first grating 14 and the second grating 15 as 0°.

In FIG. 2A, the moiré image Mo is illustrated away from the second grating 15 since the moiré fringe and the slits S are mixed and become difficult to be identified when the moiré image Mo is illustrated on the second grating 15. However, the moiré image Mo is actually formed on the second grating 15 and a downstream side thereof. Then, the moiré image Mo is photographed by the X-ray detector 16 that is disposed right under the second grating 15.

Further, as illustrated in FIG. 2A, when the subject H exists between the X-ray source 11a and the first grating 14 (that is, on the subject rest 13 of FIG. 1), the phase of the X-ray is shifted by the subject H so that the moiré fringes of the moiré image Mo are disturbed with a margin of the subject being a boundary. In the meantime, while the illustration thereof is omitted, the moiré image Mo with only the moiré fringes appears when there is no subject H between the X-ray source 11a and the first grating 14. Further, because the moiré image Mo is disturbed when an object is disposed in front of the second grating 15, the subject H is disposed in front and back of the first grating 14 and coherent X-ray is irradiated from the X-ray source 11a. The above is the principle of the Talbot interferometer and the Talbot-Lau interferometer.

Based on the principle, the second grating 15 is disposed at the position where the self image of the first grating 14 is formed within a second cover unit 130 also in the X-ray Talbot photographing device 1 according to the embodiment as illustrated in FIG. 1, for example. Further, as described above, the moiré image Mo (see FIG. 2A) becomes blurred when the second grating 15 and the X-ray detector 16 are isolated, so that the X-ray detector 16 is disposed right under the second grating 15 in the embodiment.

The second cover unit 130 is provided to protect the X-ray detector 16 and the like so that persons and objects do not collide with or contact the first grating 14, the second grating 15, the X-ray detector 16, and the like.

While not illustrated, the X-ray detector 16 is formed such that conversion elements that generate electric signals according to the irradiated X-ray are disposed two-dimensionally (in matrix), and the electric signals generated by the conversion elements are read out as image signals. Further, in the embodiment, the X-ray detector 16 photographs the moiré image Mo as the X-ray image formed on the second grating 15 as the image signals of each of the conversion elements.

Further, in the embodiment, the X-ray Talbot photographing device 1 photographs a plurality of moiré images Mo by using the so-called fringe scanning method. That is, the X-ray Talbot photographing device 1 according to the embodiment photographs a plurality of moiré images Mo by shifting the relative positions of the first grating 14 and the second grating 15 in the x-axis direction (that is, the direction orthogonal to the extending direction (y-axis direction) of the slits S) in FIG. 1 to FIG. 2A.

Then, the absorption image, the differential phase image, and the small-angle scattering image are to be reconstructed based on the plurality of moiré images Mo with the image processing done by the image processing device 2 that has received the image signals for the plurality of moiré images Mo from the X-ray Talbot photographing device 1.

Therefore, a shifting device or the like, not illustrated, for shifting the first grating 14 in the x-axis direction by a prescribed amount is provided in order to photograph the plurality of moiré images Mo by the X-ray Talbot photographing device 1 by the fringe scanning method. It is also possible to employ a configuration in which the second grating 15 is shifted instead of shifting the first grating 14 or both are shifted.

Further, it is also possible to employ a configuration in which a single moiré image Mo is photographed by the X-ray Talbot photographing device 1 while fixing the relative positions of the first grating 14 and the second grating 15, and the absorption image and the differential phase image are reconstructed by performing analysis or the like of the moiré image Mo by using the Fourier transform method or the like in the image processing performed by the image processing device.

Further, when using this method, it is not essential to provide the shift device or the like in the X-ray Talbot photographing device 1. The present disclosure is also applied to the X-ray Talbot photographing device having no such shift device.

The first grating 14 and the second grating 15 are fabricated by alternately disposing a material of high X-ray transmittance and a material of low X-ray transmittance, and it is known that the signal intensities vary between the differential phase image and the small-angle scattering image depending on the angle (angle between the subject and grating) formed between the slit line direction of the first grating 14 and the second grating 15 (y-direction in FIG. 1) and the subject structure. As illustrated in FIG. 2B, a subject H1 whose bones extend in the x-direction and a subject H2 whose bones extend in the y-direction are considered as the subject H. The reconstructed image R1 is a small-angle scattering image or a differential phase image of the subject H1 where the angle between the subject and the grating is 90° and the detected signal intensity is 0. The reconstructed image R2 is a small-angle scattering image or a differential phase image of the subject H2 where the angle between the subject and the grating is 0° and the detected signal intensity is 1.

As illustrated in FIG. 3, when measuring the image signal intensity ratio of the reconstructed image acquired by rotating the same subject with respect to the slit direction of the grating to change the angle between the subject and the grating slit to have the signal intensity of 1 in the slit parallel direction, the image signal intensity ratio is decreased by forming a cos curve and reaches 0 in the direction of 90° that is orthogonal to the slits.

Configurations of other components of the X-ray Talbot photographing device 1 will be described. In the embodiment, the X-ray Talbot photographing device 1 is the so-called vertical type, and the X-ray generator 11, the source grating 12, the subject rest 13, the first grating 14, the second grating 15, and the X-ray detector 16 are disposed in this order in the z-direction that is the gravity direction. That is, in the embodiment, the z-direction is the irradiation direction of the X-ray from the X-ray generator 11.

As an X-ray source 11a, the X-ray generator 11 includes a Coolidge X-ray source, a rotating anode X-ray source, or the like used widely in the medical setting. Further, it is also possible to use other X-ray sources as well. The X-ray generator 11 is designed to irradiate the X-ray in a cone beam form from the focal point. That is, the X-ray is irradiated to spread as leaving away from the X-ray generator 11.

Further, in the embodiment, the source grating 12 is provided underneath the X-ray generator 11. At that time, the source grating 12 in the embodiments is not attached to the X-ray generator 11 but attached to a fixing member 18a that is attached to the base 18 provided to the support 17 so that oscillation of the X-ray generator 11 generated by rotation and the like of the anode of the X-ray source 11a is not transmitted to the source grating 12.

In the embodiment, a buffer member 17a is provided between the X-ray generator 11 and the support 17 so that oscillation of the X-ray generator 11 is not propagated to other components of the X-ray Talbot photographing device 1 such as the support 17 (or so that the propagated oscillation is reduced further).

In the embodiment, in addition to the source grating 12, a filter (also referred to as an additional filter) 112 for changing the quality of the X-ray transmitted through the source grating 12, an irradiation field limiter 113 for limiting the irradiation field of the X-ray to be irradiated, an irradiation field lamp 114 and the like for performing positioning by irradiating visible light to the subject instead of the X-ray before irradiating the X-ray are attached to the fixing member 18a.

It is not essential for the source grating 12, the filter 112, and the irradiation field limiter 113 to be provided in this order. Further, in the embodiment, a first cover unit 120 is provided around the source grating 12 and the like for protecting those.

The source grating 12, the first grating 14, and the second grating 15 are held by a grating holder (not illustrated) that disposes each of the gratings in a posture along the horizontal direction. When shifting the first grating 14 and the second grating 15 at the time of photographing using the fringe scanning method described above, the grating holder itself is operated to shift the first grating 14 and the second grating 15.

A fixing unit (not illustrated) that fixes the position of the subject H with respect to the X-ray irradiated from the X-ray generator 11 is provided to the subject rest 13. The fixing unit includes a fixing part capable of fixing the subject H at a prescribed position, and a shifting mechanism capable of shifting the fixing part on a prescribed curve in a plane substantially orthogonal to the irradiation direction (z-direction) of the X-ray. By using such fixing unit, the same body part of the subject H can be photographed accurately for a plurality of times by the X-ray Talbot photographing device 1 while changing the subject set angle. In the embodiment, the subject set angle of the subject H is adjusted by the shifting mechanism of the fixing unit. However, it is also possible to employ a configuration in which the X-ray source 11a, the source grating 12, the first grating 14, the second grating 15 (may also be the grating holder), and the X-ray detector 16 rotate around the subject rest 13 to continuously photograph the subject H from a plurality of directions.

The subject set angles are the relative angles of each of the grating slit directions (extending directions of the slits S) of the source grating 12, the first grating 14, the second grating 15 with respect to the subject H in the horizontal direction. The transmission amount of the X-ray varies depending on such subject set angles, so that images observed vary depending on the angles when generated as the reconstruction images. Therefore, it is possible to acquire image sets of three kinds of reconstruction images based on the same moiré image Mo for each of a plurality of angles through photographing the same part of the subject H for a plurality of times by changing the subject set angle, so that the subject H can be accurately diagnosed.

Regarding Image Processing Device

As illustrated in FIG. 1, the image processing device 2 generates three kinds of high-definition reconstructed images (absorption image, differential phase image, and small-angle scattering image) of the subject H by an operation input of an operator (medical doctor, medical engineer) via an operation unit 22 by using the moiré image Mo acquired by the X-ray Talbot photographing device 1, calculates bone characteristic indicators and bone strength indicators from the acquired reconstruction images, and displays those indicators on a display unit 23.

Figure 4:
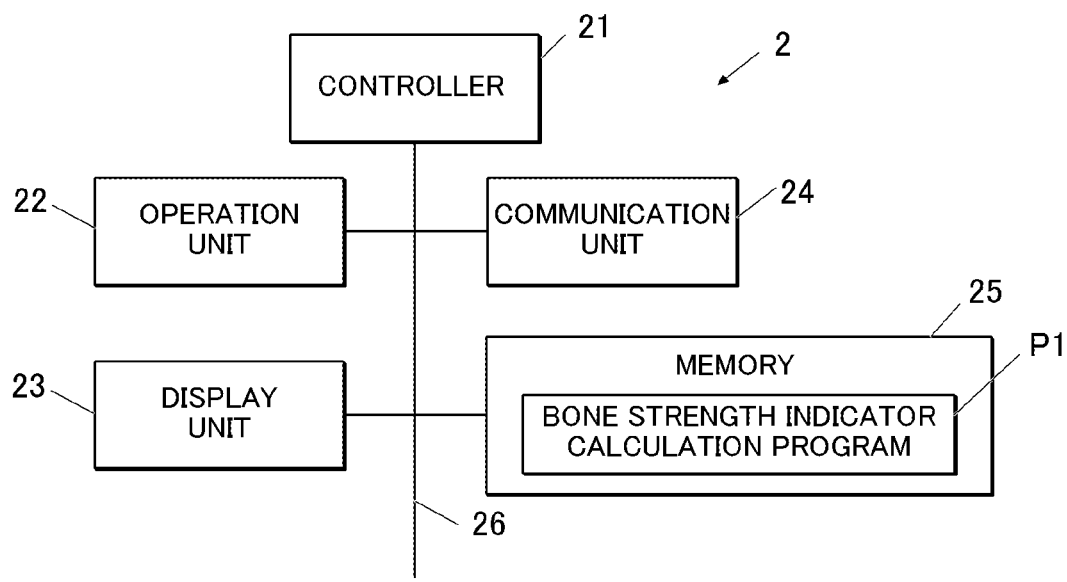
FIG. 4 is a block diagram illustrating a functional configuration of an image processing device.

Referring to FIG. 4, an internal configuration of the image processing device 2 will be described. FIG. 4 is a block diagram illustrating a functional configuration of the image processing device 2. The image processing device 2 includes a controller 21, the operation unit 22, the display unit 23, a communication unit 24, and a memory 25 as first, second, and third bone characteristic indicator calculation units and generation units. Each of the units of the image processing device 2 is connected via a bus 26.

The controller 21 is formed with a CPU (Central Processing Unit), a RAM (Random Access memory), and the like, and executes various kinds of processing such as bone strength indicator calculation processing to be described later in cooperation with programs stored in the memory 25.

The operation unit 22 includes a keyboard having a cursor key, number input keys, various function keys, and the like, and a pointing device such as a mouse, and outputs pressing signals of the keys pressed on the keyboard and operation signals by the mouse to the controller 21 as input signals. Further, the operation unit 22 may include a touch panel formed integrally with a display of the display unit 23, generate the operation signals according to the operation of those, and output the operation signals to the controller 21.

The display unit 23 includes a display such as a CRT (Cathode Ray Tube), LCD (Liquid Crystal Display), or the like, and displays an operation screen, operation state of the X-ray Talbot photographing device 1, generated reconstructed images, the bone characteristic indicators as the bone factors, the bone strength indicators indicating the bone strength, and the like according to display control of the controller 21.

The communication unit 24 includes a communication interface, and communicates with the X-ray Talbot photographing device 1 on a communication network and external systems such as PACS (Picture Archiving and Communication System) and the like through wire or wireless.

The memory 25 stores the programs to be executed by the controller 21 and data necessary for executing the programs. Stored are image data (moiré image data) of the moiré image Mo photographed by the X-ray Talbot photographing device 1, reconstructed image data, the bone characteristic indicators, the bone strength indicators, and the like.

Further, as the programs stored in the memory 25, a bone strength indicator calculation program P1 for executing the bone strength indicator calculation processing to be described later is included.

The image processing device 2 is capable of setting photographing conditions when performing X-ray Talbot photographing for the X-ray source 11a. That is, the photographing conditions when performing the X-ray Talbot photographing such as tube voltage, tube current, irradiation time (or irradiation mAs value), filter type of the filter 112 to be used, subject magnification rate and the like determined based on the body thickness of the subject and the device configuration can be set on the image processing device 2. Further, setting of such photographing conditions can be saved by being linked in advance with condition keys of the operation unit 22 provided for operating the image processing device 2.

Explanation of Operation of X-ray Photographing System

Figure 5:
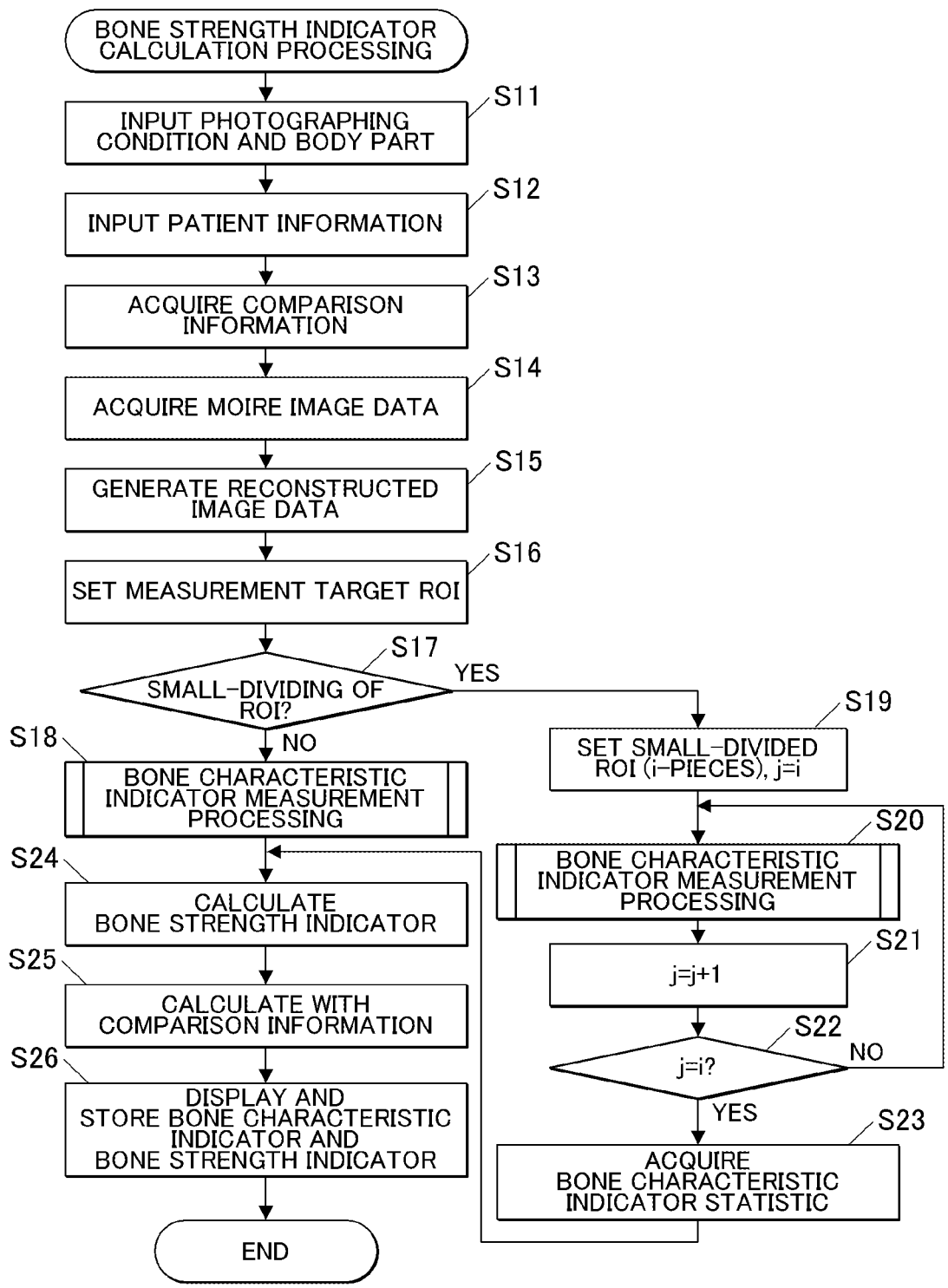
FIG. 5 is a flowchart illustrating bone strength indicator calculation processing.
Figure 6:
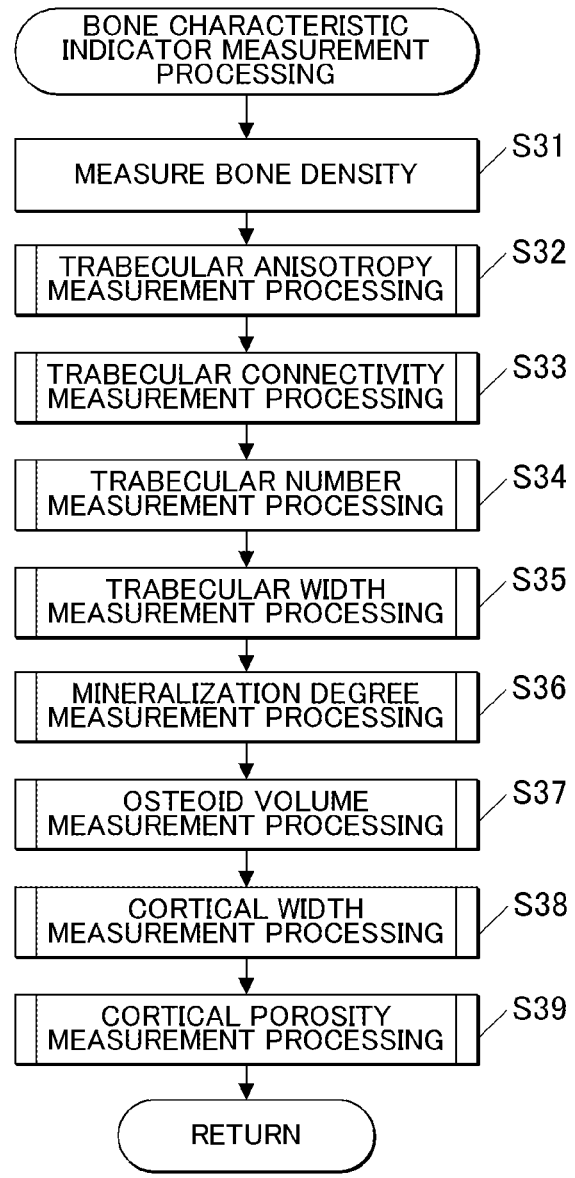
FIG. 6 is a flowchart illustrating bone characteristic indicator measurement processing.
Figure 7:
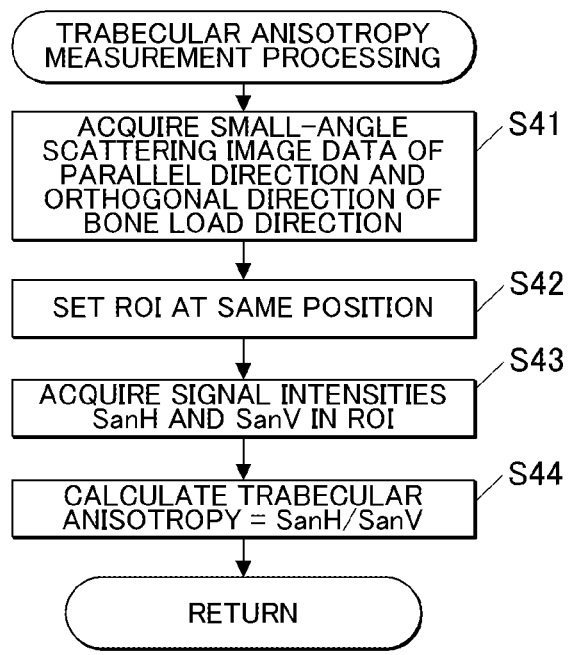
FIG. 7 is a flowchart illustrating trabecular anisotropy measurement processing.
Figure 8:
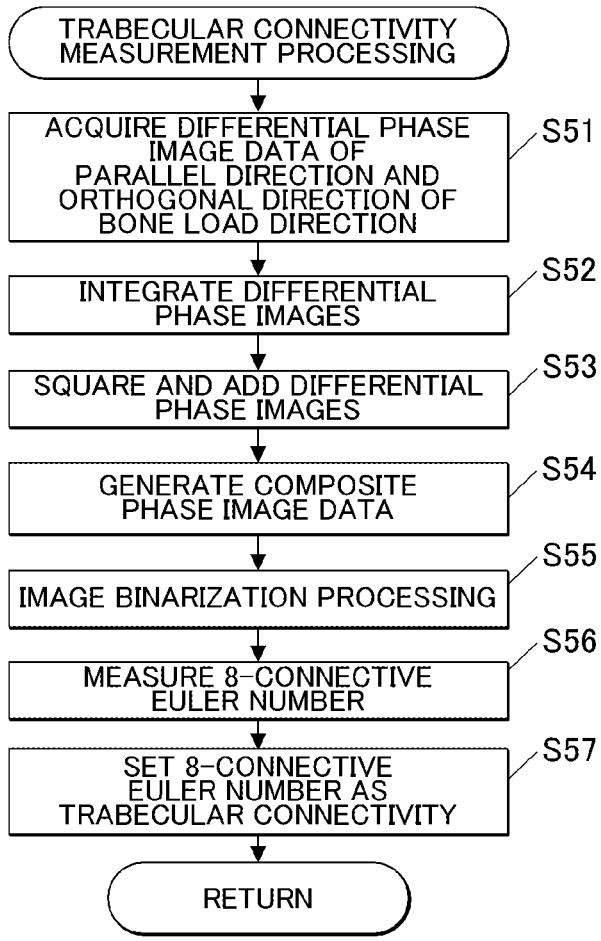
FIG. 8 is a flowchart illustrating trabecular connectivity measurement processing.
Figure 9:
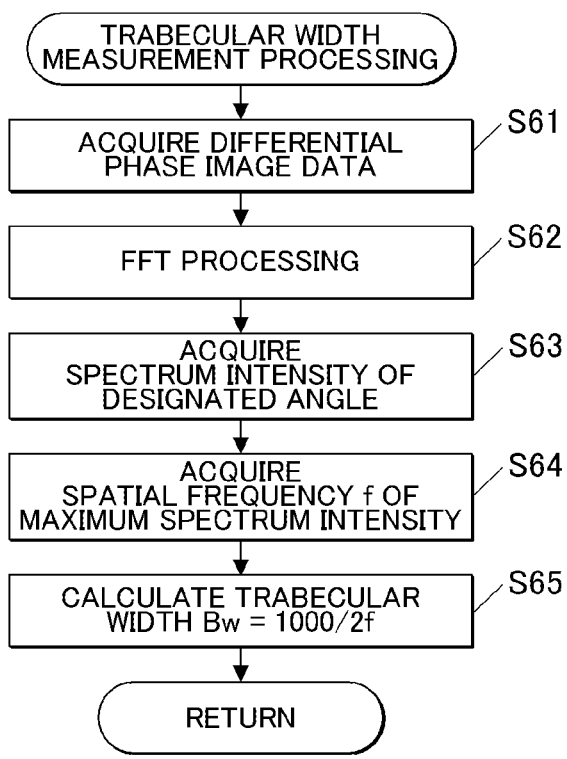
FIG. 9 is a flowchart illustrating trabecular width measurement processing.
Figure 10:
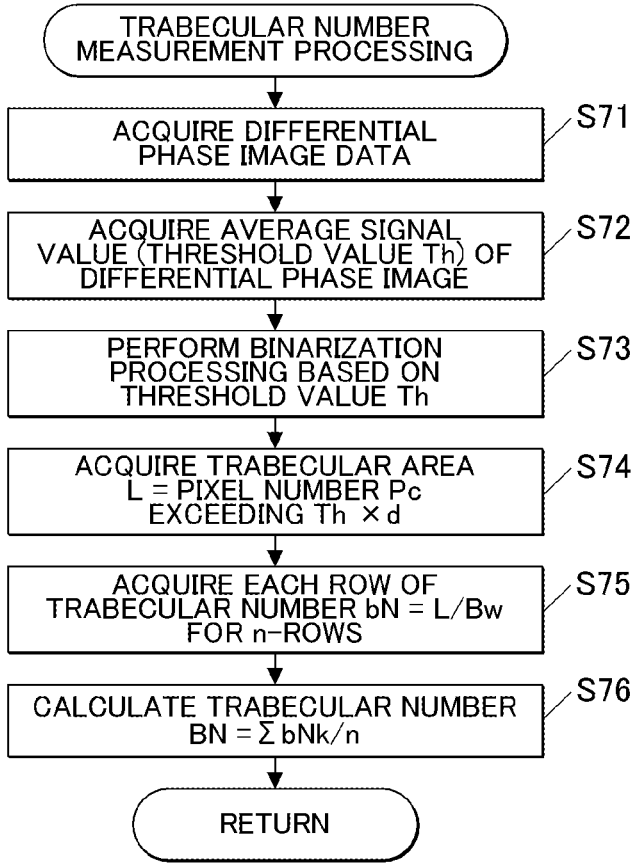
FIG. 10 is a flowchart illustrating trabecular number measurement processing.
Figure 11:
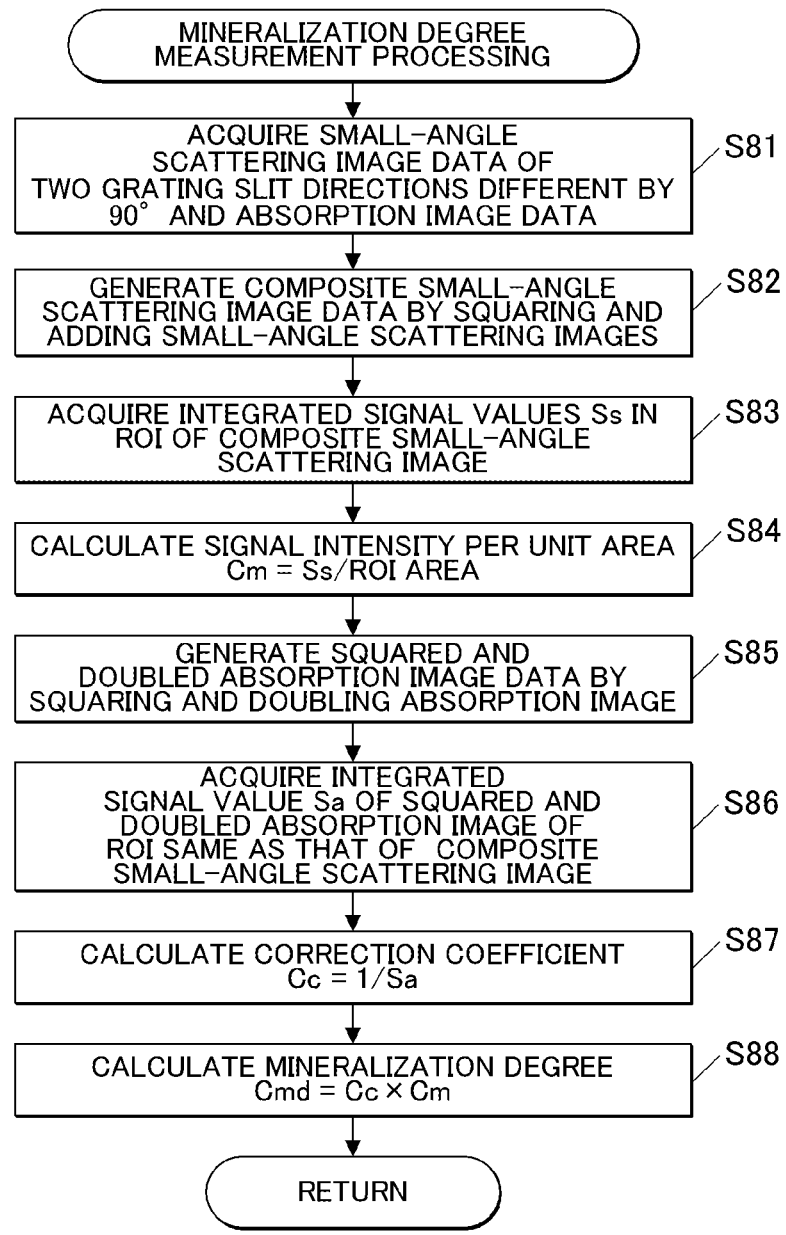
FIG. 11 is a flowchart illustrating mineralization degree measurement processing.
Figure 12:
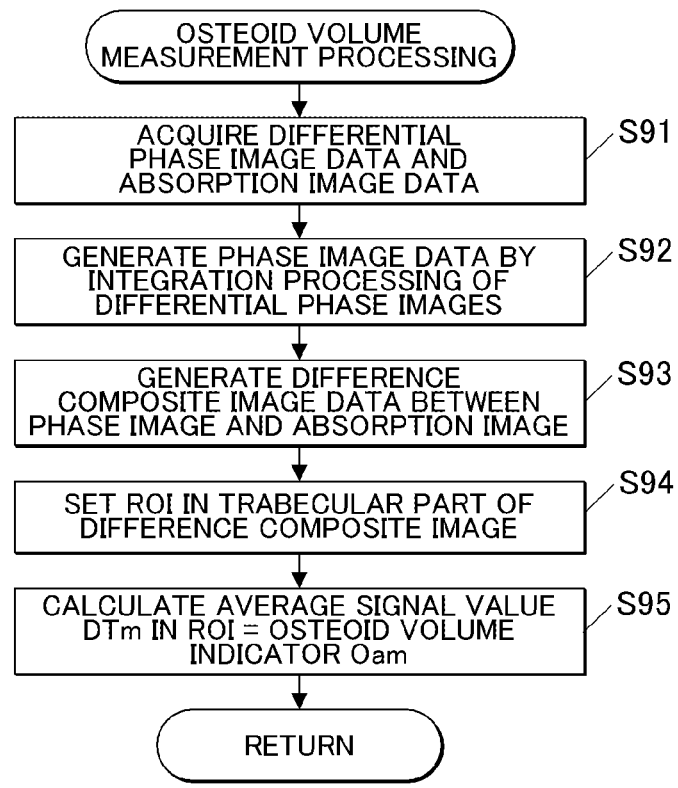
FIG. 12 is a flowchart illustrating osteoid volume measurement processing.
Figure 13:
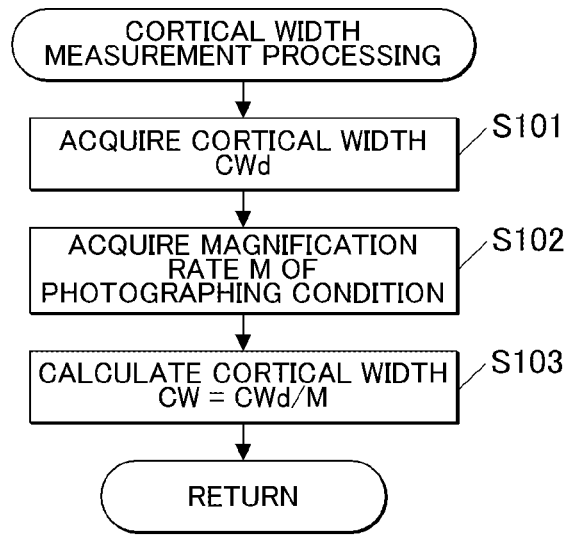
FIG. 13 is a flowchart illustrating cortical width measurement processing.
Figure 14:
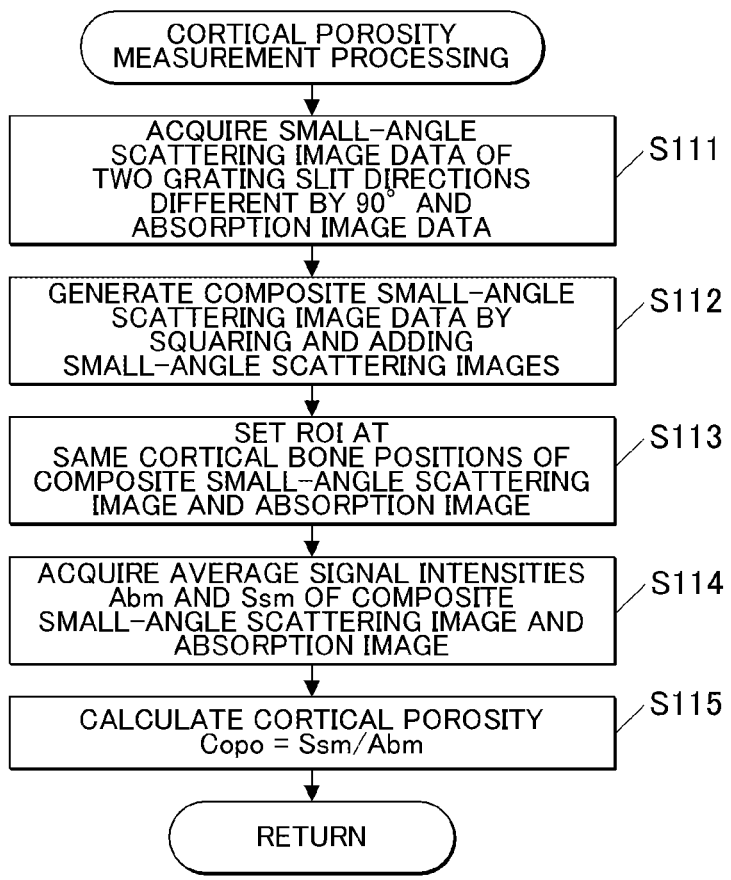
FIG. 14 is a flowchart illustrating cortical porosity measurement processing.

Referring to FIG. 5 to FIG. 21B, operations of the X-ray photographing system 100, especially operations of the image processing device 2 will be described. FIG. 5 is a flowchart illustrating the bone strength indicator calculation processing. FIG. 6 is a flowchart illustrating bone characteristic indicator measurement processing. FIG. 7 is a flowchart illustrating trabecular anisotropy measurement processing. FIG. 8 is a flowchart illustrating trabecular connectivity measurement processing. FIG. 9 is a flowchart illustrating trabecular width measurement processing. FIG. 10 is a flowchart illustrating trabecular number measurement processing. FIG. 11 is a flowchart illustrating mineralization degree measurement processing. FIG. 12 is a flowchart illustrating osteoid volume measurement processing. FIG. 13 is a flowchart illustrating cortical width measurement processing. FIG. 14 is a flowchart illustrating cortical porosity measurement processing.

Figure 15:
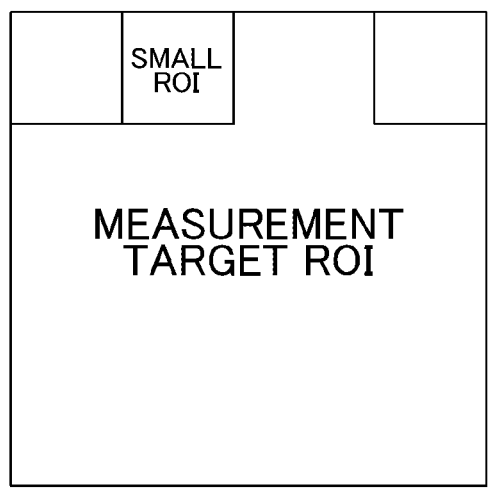
FIG. 15 is a view illustrating a measurement target ROI divided into small ROIs.
Figure 16A:
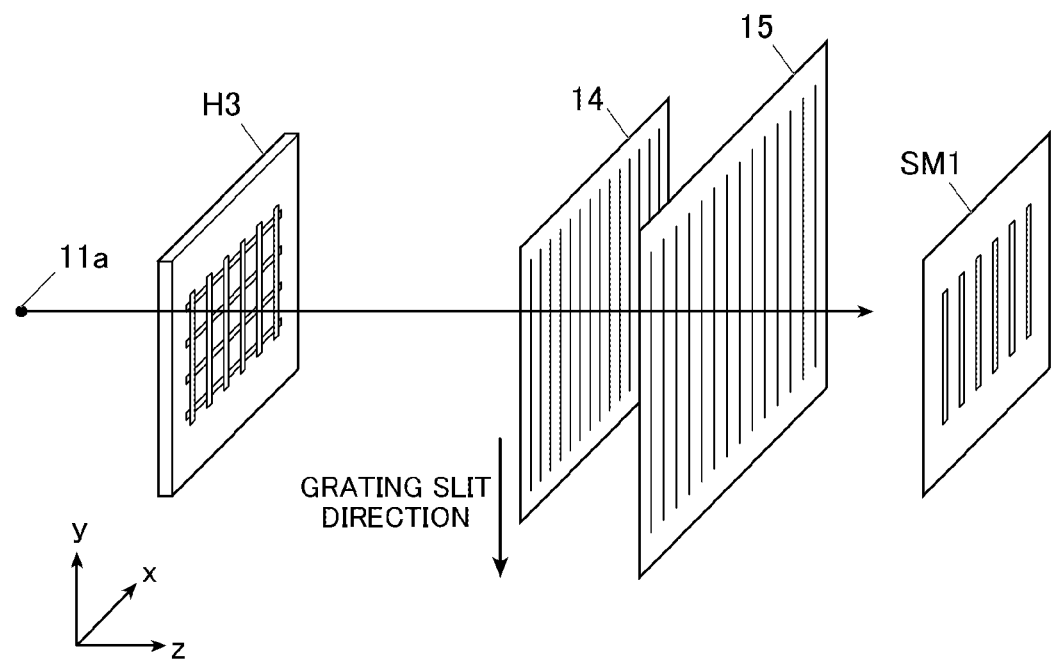
FIG. 16A is a view illustrating a small-angle scattering image acquired by photographing a subject of a mesh-like structure at a prescribed grating slit direction.
Figure 16B:
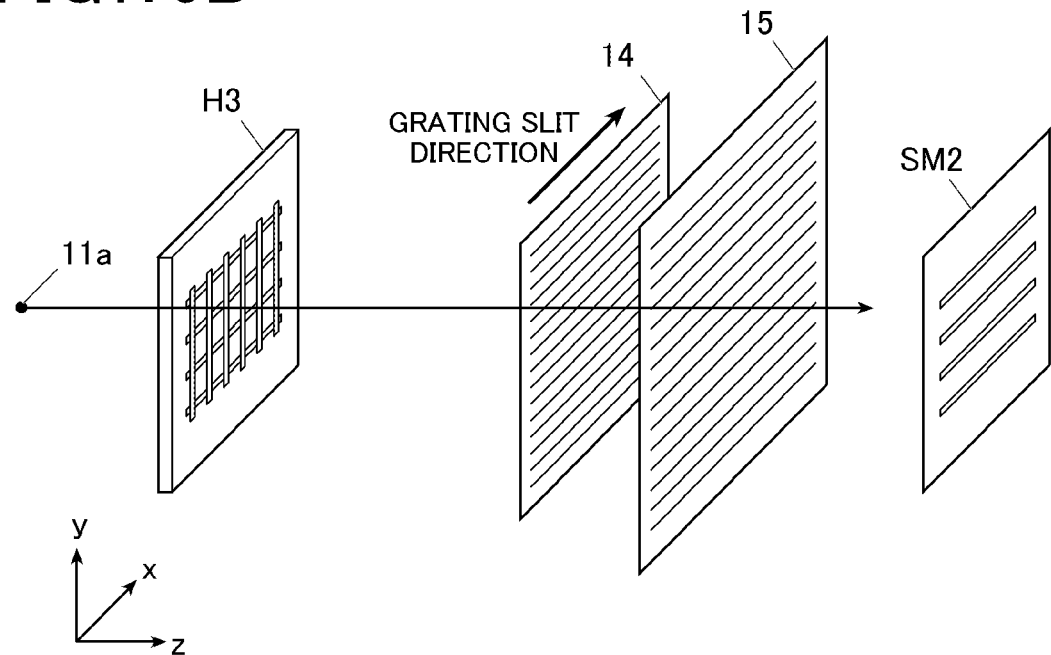
FIG. 16B is a view illustrating a small-angle scattering image acquired by photographing the subject by rotating the grating slit direction of FIG. 16A by 90°.
Figure 17:
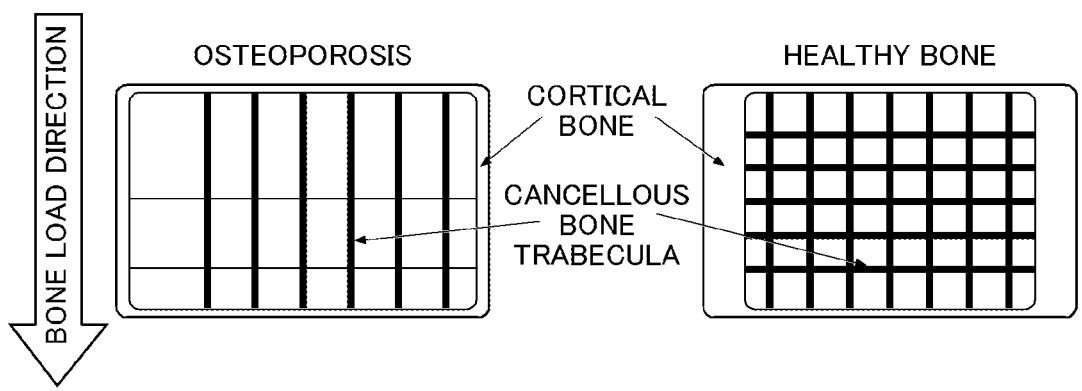
FIG. 17 illustrates schematic views of bones of an osteoporosis patient and a healthy person and a relation thereof with respect to the bone load direction.
Figure 18A:
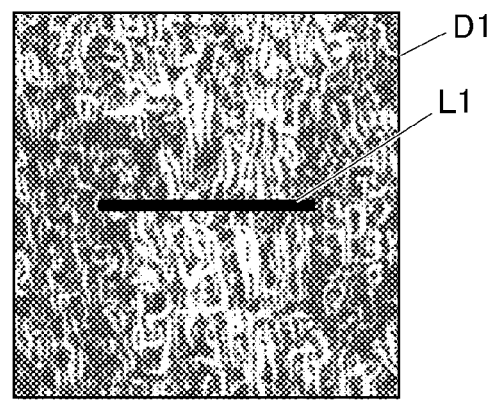
FIG. 18A is a differential phase image after integration processing.
Figure 18B:
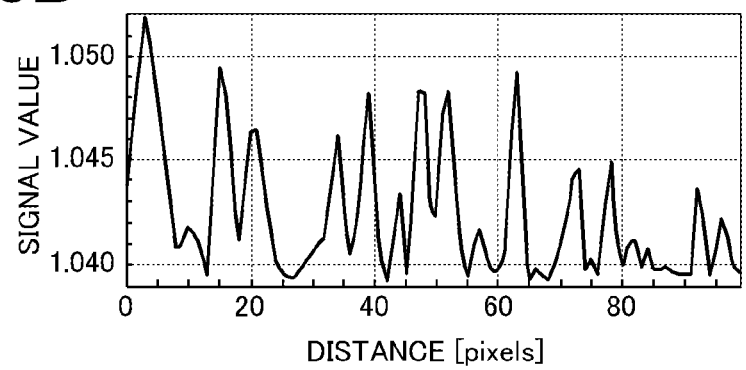
FIG. 18B is a graph illustrating signal values with respect to distance of a straight line of the differential phase image after the integration processing.
Figure 18C:
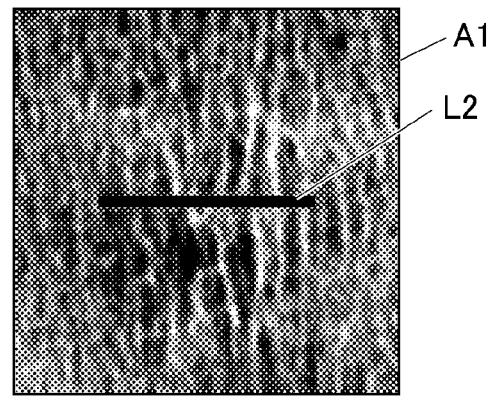
FIG. 18C is an absorption image.
Figure 18D:
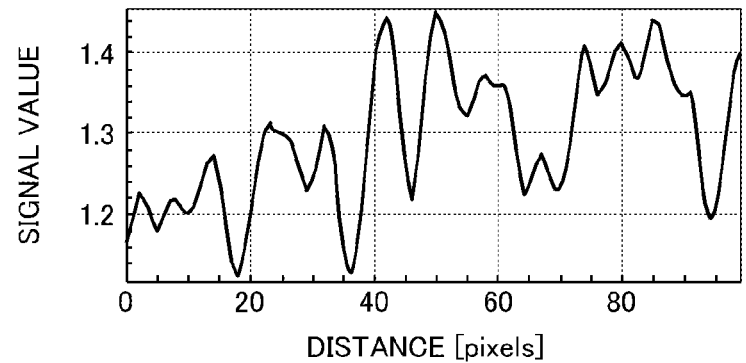
FIG. 18D is a graph illustrating signal values with respect to distance of a straight line of the absorption image.

FIG. 15 is a view illustrating a measurement target ROI divided into small ROIs. FIG. 16A is a view illustrating a small-angle scattering image SM1 acquired by photographing a subject H3 of a mesh-like structure in a prescribed grating slit direction. FIG. 16B is a view illustrating a small-angle scattering image SM2 acquired by photographing the subject H3 by rotating the grating slit direction of FIG. 16A by 90°. FIG. 17 illustrates schematic views of the bones of an osteoporosis patient and a healthy person and a relation thereof with respect to the bone load direction. FIG. 18A is a differential phase image D1 after integration processing. FIG. 18B is a graph illustrating signal values with respect to distance of a straight line L1 of the differential phase image D1 after the integration processing. FIG. 18C is an absorption image A1. FIG. 18D is a graph illustrating signal values with respect to distance of a straight line L2 of the absorption image A1.

Figure 19A:
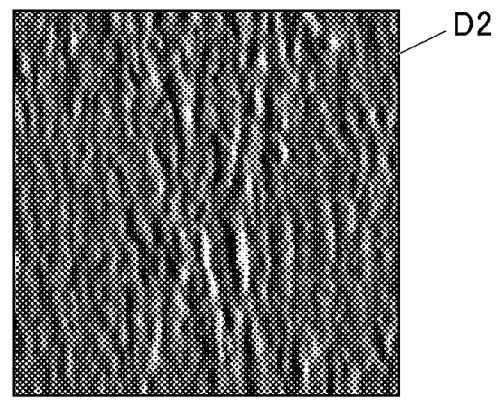
FIG. 19A is a differential phase image.
Figure 19B:
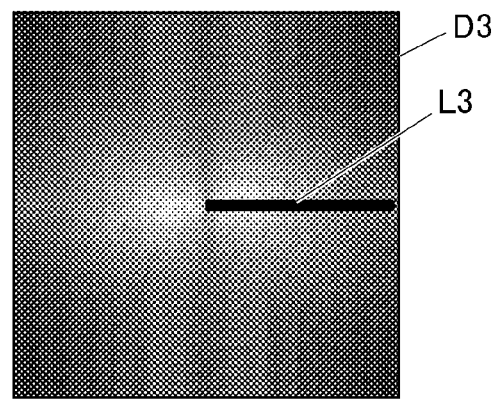
FIG. 19B is a differential phase image after two-dimensional FFT processing.
Figure 19C:
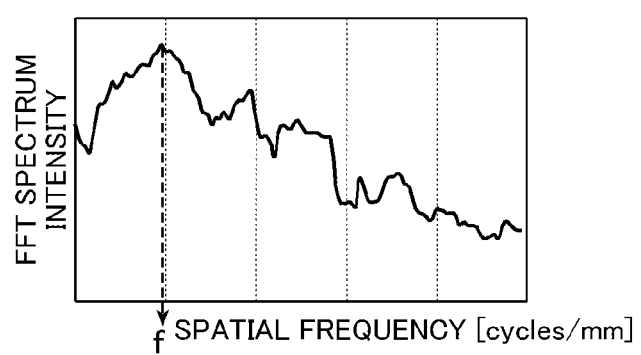
FIG. 19C is a graph illustrating spectrum intensities with respect to space frequencies on a straight line of the differential phase image after the two-dimensional FFT processing.
Figure 20A:
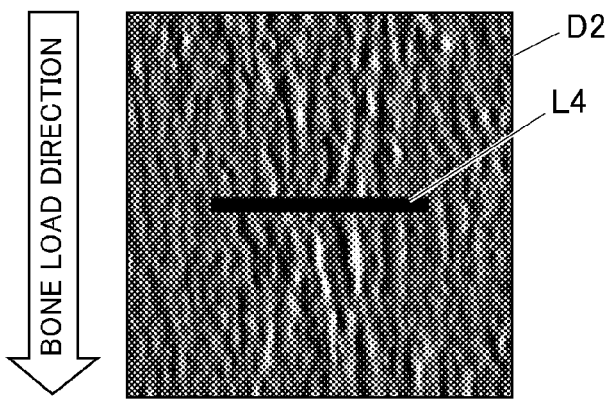
FIG. 20A is a differential phase image.
Figure 20B:
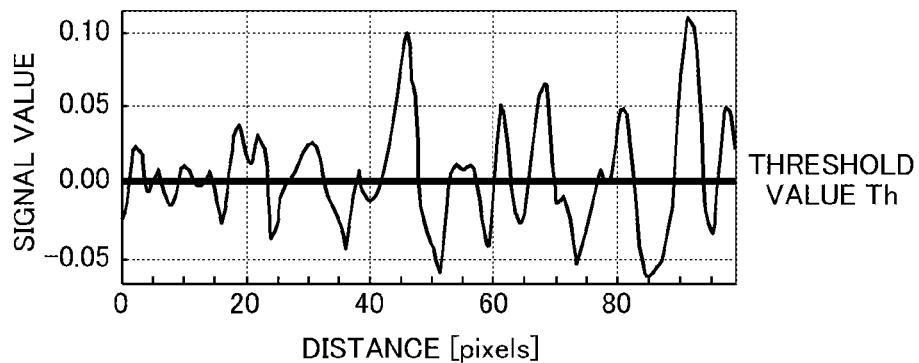
FIG. 20B is a graph illustrating signal values with respect to distance of a straight line of the differential phase image.
Figure 20C:
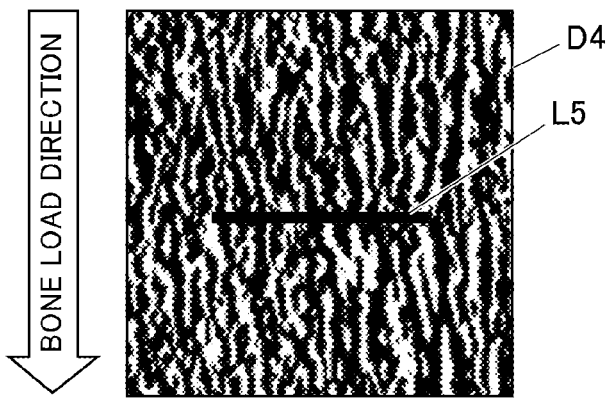
FIG. 20C is a differential phase image after binarization.
Figure 20D:
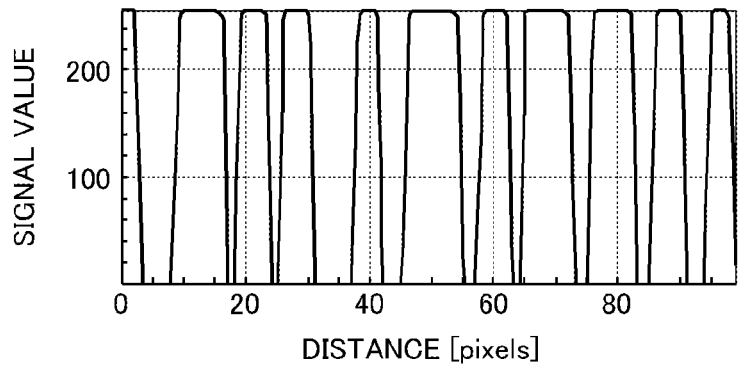
FIG. 20D is a graph illustrating signal values with respect to distance of a straight line of the differential phase image after the binarization.
Figure 21A:
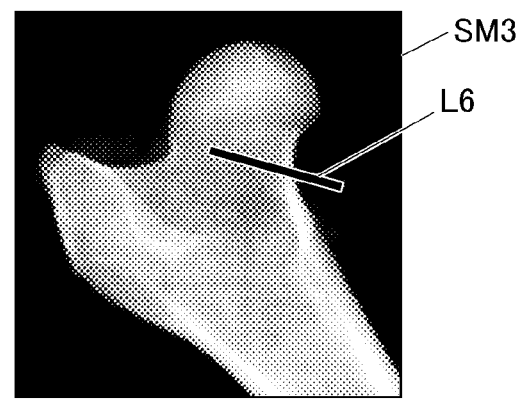
FIG. 21A is a small-angle scattering image.
Figure 21B:
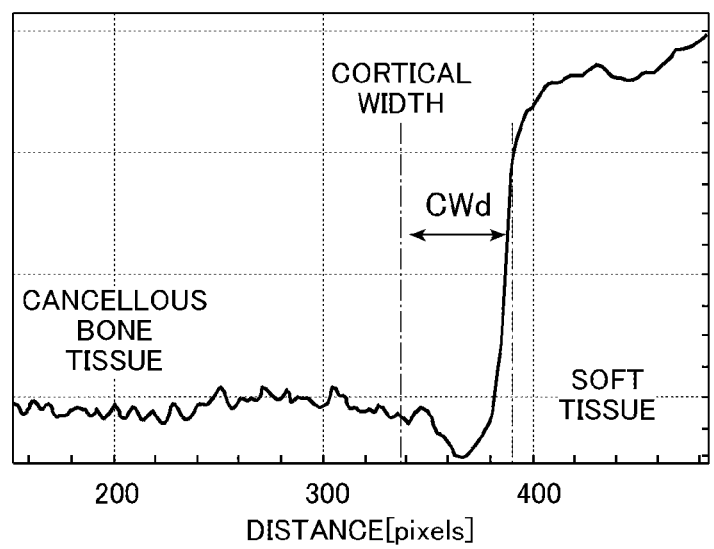
FIG. 21B is a graph illustrating signal values with respect to distance of a part of a straight line of the small-angle scattering image.

FIG. 19A is a differential phase image D2. FIG. 19B is a differential phase image D3 after two-dimensional FFT (Fast Fourier Transform) processing. FIG. 19C is a graph illustrating FFT spectrum intensities with respect to space frequencies on a straight line L3 of the differential phase image D3 after the two-dimensional FFT processing. FIG. 20A is a differential phase image D2. FIG. 20B is a graph illustrating signal values with respect to distance of a straight line L4 of the differential phase image D2. FIG. 20C is a differential phase image D4 after binarization. FIG. 20D is a graph illustrating signal values with respect to distance of a straight line L5 of the differential phase image D4 after the binarization. FIG. 21A is a small-angle scattering image SM3. FIG. 21B is a graph illustrating signal values with respect to distance of a part of a straight line L6 of the small-angle scattering image SM3.

Referring to FIG. 5 to FIG. 21B, the bone strength indicator calculation processing executed by the image processing device 2 will be described. The bone strength is defined by following expression (1). Bone strength=bone density+bone quality (bone microstructure, bone turnover state, bone micro-fracture, bone tissue mineralization degree) - - - (1) Further, definition of physical interpretation of the bone strength is expressed by following expression (2). Bone strength=material factors (volume of bone mineral such as Ca, volume of osteoid, composition ratio)+structural factors (thickness and structure of trabecula/cortical bones) - - - (2)

Further, the bone density is the volume of the bone mineral per unit area/cubic volume. The bone microstructure is microstructure factors such as the trabecular width, the number, the trabecular connectivity, the anisotropy of the cancellous bones as well as the width, the porosity, and the like of the cortical bones. The bone turnover is a cycle of destructive absorption of old bones and generation of new bones. There is a cycle of absorption of old bones→formation of osteoid (precursor of bones)→mineralization of osteoid→completion of mineralization (completion of bones)→absorption of bones. A drug for treatment of osteoporosis works on the turnover to facilitate formation of the bones and to suppress absorption of the bones so as to increase the bones.

In the image processing device 2, the controller 21 executes the bone strength indicator calculation processing according to the bone strength indicator calculation program P1 stored in the memory 25 by taking an input of an execution command of the bone strength indicator calculation processing from the operator via the operation unit 22 as a trigger, for example.

As illustrated in FIG. 5, first, the controller 21 receives input of the photographing conditions and a body part of a patient as the subject to be photographed from the operator via the operation unit 22 (step S11). One each of three kinds of reconstructed image data (absorption image data, differential phase image data, and small-angle scattering image data) is generated from moiré image data of prescribed pieces (four pieces, for example). In the embodiment, for example, it is assumed to input the photographing conditions for performing photographing of a prescribed pieces of moiré images by setting the grating slit direction of the first grating 14 and the second grating 15 to the parallel direction of the bone load direction of the subject and photographing of a prescribed pieces of moiré images by setting the grating slit direction of the first grating 14 and the second grating 15 to the orthogonal direction (direction different by 90°) of the bone load direction of the subject. The bone load direction of the patient as the subject is the direction along which the load is imposed upon the patient in a daily life. Normally, the vertical direction along which the gravity works in a standing state is defined as the bone load direction.

Then, the controller 21 acquires patient information of the patient as the subject according to the input from the operator via the operation unit 22 (step S12). The patient information contains typical patient information such as ID and age of the patient and also information indicating whether or not to perform small-dividing of measurement target ROI (Region Of Interest). The photographing conditions together with the patient information are defined as image conditions.

Then, the controller 21 reads out and acquires comparison information stored in advance in the memory 25 (step S13). The comparison information contains bone characteristic indicators of those of the same age as that of the patient, the average value of the bone strength indicators, and measurement values of the past read out from an age-parameter (bone characteristic indicators, bone strength indicators) table stored in the memory 25, for example. The bone characteristic indicators are defined as the bone density, the trabecular anisotropy, the trabecular connectivity, the trabecular width, the trabecular number, the mineralization degree, the osteoid volume, the cortical porosity, and the cortical width. The trabecular anisotropy, the trabecular connectivity, the trabecular width, the trabecular number are the anisotropy, the connectivity, the width, and the number of the trabeculae. The mineralization degree is a progress degree of mineralization of bone tissues, and it is a ratio between the bone mineral and bone matrix (collagen or the like of osteoid main component). The osteoid volume is the volume of the osteoid that is one of the matrix elements of the bone tissues. The cortical porosity is the porosity of the cortical bone that is the hard bone on an outer seam. The cortical width is the width of the cortical bone.

Then, the controller 21 controls the X-ray Talbot photographing device 1 via the communication unit 24 to radiograph the patient as the subject according to the photographing conditions inputted in step S11, acquires the moiré image data of a plurality of subject set angles from the X-ray Talbot photographing device 1 via the communication unit 24, and stores the moiré image data to the memory 25 by associating the image conditions to the moiré image data (step S14). The X-ray Talbot photographing device 1 photographs the subject H according to the control of the controller 21. At this time, the same body part of the subject H is photographed for a plurality of times while changing the subject set angle.

Then, the controller 21 generates the reconstructed image data (absorption image data, differential phase image data, small-angle scattering image data) by reconstructing the moiré image data acquired in step S14, and stores the reconstructed image data in the memory 25 (step S15). At this time, it is desirable for the image signals of each of the reconstructed image data to be normalized such that the signal intensity in the air (without the subject being placed) is 1. When photographed with the photographing conditions as the example of the above, generated from the moiré image data whose grating slit direction is the parallel direction of the bone load direction and the moiré image data whose grating slit direction is the orthogonal direction of the bone load direction are five pieces of reconstructed image data that are the absorption image data whose grating slit direction is either one of the directions, differential phase image data whose grating slit directions are the two directions (parallel direction and orthogonal direction of the bone load direction), and small-angle scattering image data whose grating slit directions are the two directions (parallel direction and orthogonal direction of the bone load direction).

Then, the controller 21 displays the reconstructed image data generated in step S15 on the display unit 23, and performs setting of the measurement target ROI in the reconstructed images for each of the bone characteristic indicator measurement processing according to the input of the measurement target ROI from the operator via the operation unit 22 (step S16). As the measurement target ROI, there are ROI including cancellous bones and ROI including cortical bones. In the trabecular anisotropy measurement processing, the trabecular connectivity measurement processing, the trabecular width measurement processing, and the trabecular number measurement processing, the ROI including the cancellous bones is set and applied. In the cortical width measurement processing, and the cortical porosity measurement processing, the ROI including the cortical bones is set and applied. In the bone density measurement processing, the mineralization degree measurement processing, and the osteoid volume measurement processing, at least either one of the ROI including the cancellous bones and the ROI including the cortical bones is set and applied. Further, in step S16, also included is the input of information indicating whether or not to divide the measurement target ROI into a plurality of still smaller ROIs. For example, as illustrated in FIG. 15, the measurement target ROI is divided into a plurality of small ROIs. The bone characteristic indicator as the dividing target of the measurement target ROI is at least one out of the mineralization degree, the osteoid volume, and the cortical porosity.

Then, the controller 21 determines whether or not there is small-dividing of the measurement target ROI based on whether or not there is the input for dividing the measurement target ROI into a plurality of small ROIs in step S16 (step S17). When there is no small-dividing of the measurement target ROI (NO in step S17), the controller 21 executes the bone characteristic indicator measurement processing (step S18). The bone characteristic indicator measurement processing is the processing for automatically measuring the bone density, the trabecular anisotropy, the trabecular connectivity, the trabecular width, the trabecular number, the mineralization degree, the osteoid volume, the cortical porosity, and the cortical width as the bone characteristic indicators. It is also possible to measure the bone mineral volume instead of the bone density.

Here, the bone characteristic indicator measurement processing of step S18 will be described by referring to FIG. 6. First, the controller 21 measures the bone density through calculating signals of the measurement target ROI set in step S16 in the absorption image by using the absorption image data generated in step S15 (step S31). A measurement method of the bone density may be a method that photographs a reference object such as an aluminum step simultaneously with the bone and estimates the bone density from the signal value of the reference object corresponding to the signal value of the bone like a CXD (Computed X-ray Densitometer) method, for example, may be a method that measures the bone density from a bone signal profile area of a difference composite image of absorption images acquired by photographing a same position with two kinds of high and low X-ray energies like the so-called DEXA method, or may be a method that measures the bone density from an integrated signal value of bone regions of a division composite image of the absorption images acquired by photographing a same position with high and low energies.

Then, the controller 21 executes the trabecular anisotropy measurement processing (step S32). Here, the trabecular anisotropy measurement processing of step S32 will be described by referring to FIG. 7. First, the controller 21 acquires the small-angle scattering image data whose grating slit direction is the parallel direction of the bone load direction and the small-angle scattering image data whose grating slit direction is the orthogonal direction of the bone load direction generated in step S15 (step S41). The bone load direction may be acquired by performing anatomical feature volume extraction of a pre-photographed image of a low dose used for positioning, for example, or may be set by the operator in the pre-image. Alternatively, a marker reflected in the X-ray image for determining the grating direction or the subject set direction may be used.

Then, the controller 21 sets the measurement target ROI set in step S16 at the same position of the two pieces of small-angle scattering image data of the parallel direction and the orthogonal direction of the bone load direction acquired in step S41 (step S42).

Then, the controller 21 acquires signal value intensities SanH and SanV in the measurement target ROI set in step S42 (step S43). The signal value intensities SanH and SanV correspond to angles 0° and 90° between the subject and the grating slit of FIG. 3. The subject in the direction orthogonal to the grating slit direction is not detected in the small-angle scattering image as illustrated in FIG. 2B. The first grating 14 and the second grating 15 are disposed in a prescribed grating slit direction as illustrated in FIG. 16A and a small-angle scattering image SM1 is acquired by photographing the subject H3 of a mesh-like structure as in the case of Non-Patent Literature mentioned above, while a small-angle scattering image SM2 is acquired through photographing the subject H3 by rotating the first grating 14 and the second grating 15 of FIG. 16A by 90°. Only the signals of the grating slit parallel direction remain in the small-angle scattering images SM1 and SM2, so that the structure of the grating slit parallel direction can be extracted.

Then, the controller 21 calculates "trabecular anisotropy=SanH/SanV" by using the signal value intensities SanH and SanV acquired in step S43 (step S44), and ends the trabecular anisotropy measurement processing. Note that FIG. 17 illustrates schematic views of the bones of an osteoporosis patient and a healthy person and a relation thereof with respect to the bone load direction. In the schematic view of the bones, cortical bones and cancellous bone trabeculae are illustrated. The number of cancellous bone trabeculae in the schematic views of the bones is illustrated with the number of straight lines in the horizontal direction and perpendicular direction that are orthogonal and parallel to the bone load direction, and the width of the cancellous bone trabeculae is illustrated with the thickness of the straight lines. The volume of cortical bone is illustrated with the width of the periphery of the cancellous bone trabeculae region. The number and the width of the cancellous bone trabeculae of the osteoporosis patient are smaller than those of the healthy person. The trabecular anisotropy necessary for diagnosing osteoporosis is the trabecular anisotropy of the orthogonal and parallel directions of the bone load direction illustrated in FIG. 17, so that the bone load direction is acquired in advance and the trabecular anisotropy is calculated with the two kinds of small-angle scattering images.

Returning to FIG. 6, the controller 21 executes the trabecular connectivity measurement processing (step S33). Here, the trabecular connectivity measurement processing of step S33 will be described by referring to FIG. 8. First, the controller 21 acquires the differential phase image data whose grating slit direction is the parallel direction of the bone load direction and the differential phase image data whose grating slit direction is the orthogonal direction of the bone load direction generated in step S15 (step S51).

Then, the controller 21 performs integration processing of the measurement targets ROI acquired in step S16 for the differential phase images of the two pieces of the differential phase image data acquired in step S51 (step S52). In step S52, the differential phase image D1 after the integration processing illustrated in FIG. 18A is acquired, for example. In FIG. 18B, signal values of the straight line L1 corresponding to the distance (pixels) are illustrated as a profile on the straight line L1 of the differential phase image D1. The distance (pixels) is the distance in the right direction with the left end of the straight line being 0. For comparison, the absorption image A1 is presented in FIG. 18C. In FIG. 18D, signal values of the straight line L2 corresponding to the distance (pixels) are illustrated as a profile on the straight line L2 of the absorption image A1. In the differential phase image D1, it is possible to detect minute trabeculae that cannot be detected in the absorption image A1. The physical volume is set to be the same in the differential phase image D1 and the absorption image A1 after the integration processing.

Then, the controller 21 squares and adds the two differential phase images (phase images) integrated in step S52 (step S53). Then, the controller 21 generates composite phase image data having the integrated differential phase image squared and added in step S53 (step S54). Then, the controller 21 performs binarization processing of the composite phase image of the composite phase image data generated in step S54 using the prescribed threshold value (step S55).

Then, the controller 21 measures 8-connective Euler number from the binarized composite phase image acquired in step S55 (step S56). Then, the controller 21 sets the 8-connective Euler number measured in step S56 as the trabecular connectivity (step S57), and ends the trabecular connectivity measurement processing.

Returning to FIG. 6, the controller 21 executes the trabecular width measurement processing (step S34). Here, the trabecular width measurement processing of step S34 will be described by referring to FIG. 9. First, the controller 21 acquires one (for example, the grating slit direction is the orthogonal direction of the bone load direction) of the differential phase image data generated in step S15 (step S61). For example, the differential phase image data of the differential phase image D2 illustrated in FIG. 19A is acquired. Then, the controller 21 performs two-dimensional FFT processing on the region of the measurement target ROI set in step S16 of the differential phase image of the one differential phase image data acquired in step S61 to generate the FFT-processed differential phase image data (two-dimensional FFT image data) (step S62). For example, generated is the differential phase image data of the FFT-processed differential phase image D3 illustrated in FIG. 19B.

Then, the controller 21 acquires the (FFT) spectrum intensities of the designated angle to be the representative of the FFT-processed differential phase image acquired in step S62 (step S63). For example, as illustrated in FIG. 19C, the (FFT) spectrum intensities on the straight line L3 with respect to the spatial frequency (cycles/mm) are obtained as a profile on the straight line L3 of the designated angle of the FFT-processed differential phase image D3 of FIG. 19A.

Then, the controller 21 acquires a spatial frequency f exhibiting the maximum intensity in the spectrum intensities of the spatial frequencies of 1 to 10 (cycles/mm) corresponding to the trabecular width range of 50 to 500 (μm) among the spectrum intensities of the designated angle acquired in step S63 (step S64). Then, the controller 21 calculates "trabecular width Bw=1000/2f (μm)" by using the spatial frequency f acquired in step S64 (step S65), and ends the trabecular width measurement processing.

The trabecular width measurement processing may also be configured such that the two pieces of differential phase image data whose grating slit directions are different by 90° are acquired in step S61, the composite differential phase image data acquired by squaring and adding the two pieces of differential phase images is generated, and the processing of steps S62 to S65 is executed on the squared and added composite differential phase image data.

Returning to FIG. 6, the controller 21 executes the trabecular number measurement processing (step S35). Here, the trabecular number measurement processing of step S35 will be described by referring to FIG. 10. First, the controller 21 acquires one (for example, the grating slit direction is the orthogonal direction of the bone load direction) of the differential phase image data generated in step S15 (step S71). Then, the controller 21 acquires an average signal value of the measurement target ROI set in step S16 of the differential phase image of the one piece of the differential phase image data acquired in step S71 as a threshold value Th (step S72). For example, the differential phase image data of the differential phase image D2 illustrated in FIG. 20A is acquired. Signal values of a straight line L4 with respect to the distance (pixels) are illustrated in FIG. 20B as a profile on the straight line L4 of the differential phase image D2. The average value of the signal values of the profile in FIG. 20B is taken as the threshold value Th.

Then, the controller 21 performs binarization processing of the differential phase image of the measurement target ROI set in step S16 of one piece of the differential phase image data acquired in step S71 based on the threshold value Th acquired in step S72 (step S73). For example, generated is the differential phase image data of the binarized differential phase image D4 illustrated in FIG. 20C. Out of the differential phase image D4, signal values of a straight line L5 with respect to the distance (pixels) are illustrated in FIG. 20D as a profile on the straight line L5 in the direction orthogonal to the trabecula desired to be measured in the differential phase image D4.

Then, the controller 21 reads out detector pixel size d stored in advance in the memory 25, measures pixel number Pc exceeding the threshold value Th (number of pixels with which the signal value in the profile on the straight line L4 is 1) of the binarized differential phase image acquired in step S73, and calculates "trabecular area L=Pc×d" (step S74). Then, the controller 21 acquires "trabecular number bN=L/Bw" of each row of the differential phase image of the measurement target ROI acquired in step S16 for n-rows by using the trabecular area L acquired in step S74 and the trabecular width Bw calculated in step S65 (step S75). Then, the controller 21 calculates "trabecular number BN=ΣbNk/n (k=1 to n) (step S76), and ends the trabecular number measurement processing.

The trabecular number measurement processing may also be configured such that the two pieces of differential phase image data whose grating slit directions are different by 90° are acquired in step S71, the composite differential phase image data acquired by squaring and adding the two pieces of differential phase images is generated, and the processing of steps S72 to S76 is executed by using the squared and added composite differential phase image data.

Returning to FIG. 6, the controller 21 executes the mineralization degree measurement processing (step S36). Here, the mineralization degree measurement processing of step S36 will be described by referring to FIG. 11. First, the controller 21 acquires small-angle scattering image data of two directions with grating slit directions different from each other by 90° and absorption image data generated in step S15 (step S81). In the case of the photographing conditions of the example described above, acquired are the two pieces of small-angle scattering image data whose grating slit directions are the parallel direction and the orthogonal direction of the bone load direction and a single piece of the absorption image data. Then, the controller 21 squares and adds the small-angle scattering image data of two directions acquired in step S81 to generate the composite small-angle scattering image data (step S82).

Then, the controller 21 acquires an integrated signal value Ss of the measurement target ROI set in step S16 of the composite small-angle scattering image data acquired in step S82 (step S83). Then, the controller 21 calculates "signal intensity Cm per unit area=Ss/measurement target ROI area" as the mineralization degree before being corrected by using the integrated signal value Ss generated in step S82 (step S84). Then, the controller 21 squares and doubles the signal value of the absorption image of the single piece of absorption image data acquired in step S81 to generate squared and doubled absorption image data (step S85).

Then, the controller 21 acquires an integrated signal value Sa of the measurement target ROI set in step S16 of the squared and doubled absorption image data generated in step S85 (step S86). Then, the controller 21 takes a reciprocal of the integrated signal value Sa acquired in step S86 as a correction coefficient Cc (step S87). Then, the controller 21 calculates "mineralization degree Cmd=Cc×Cm" by using the correction coefficient Cc acquired in step S87 and the signal intensity Cm per unit area calculated in step S84 (step S88), and ends the mineralization degree measurement processing. The correction coefficient Cc may include an additional correction according to an image condition inputted in steps S11, S12 (to be an additional correction coefficient). For example, when photographed with a higher value than a reference tube voltage based on the X-ray energy information received as the image condition, for example, the additional correction coefficient is multiplied to "correction coefficient Cc=1/Sa" acquired from the integrated signal value Sa of the composite absorption image so that the mineralization degree becomes higher.

The mineralization degree measurement processing may also be configured such that a single piece of small-angle scattering image data is acquired in step S81, the average signal value of the small-angle scattering image is calculated as the mineralization degree Cm, and the mineralization degree Cmd is calculated in step S88. Further, it is also possible to employ a configuration in which one each of the small-angle scattering image data and absorption image data may be acquired in step S81, and the correction coefficient Cc may be calculated from the absorption image to correct the mineralization degree Cm.

Further, it is also possible to employ a configuration in which, as the reconstructed image data, two pieces of small-angle scattering image data, two pieces of differential phase image data, and two pieces of absorption image data of two directions (for example, the grating slit directions are two directions that are parallel and orthogonal to the bone load direction) with the grating slit directions different from each other by 90° in step S15 of FIG. 5. In step S81 of the mineralization degree measurement processing with such configuration, acquired are the two pieces of small-angle scattering image data and the two pieces of absorption image data of the two directions with the grating slit directions generated in step S15 different from each other by 90°. In step S85, the two pieces of absorption image data acquired in step S81 are squared and added to generate the composite absorption image data. In step S86, the integrated signal value Sa of the measurement target ROI set in step S16 of the composite absorption image data generated in step S85 is acquired. Other steps are similar to configurations of the mineralization degree measurement processing described above.

Returning to FIG. 6, the controller 21 executes the osteoid volume measurement processing (step S37). Here, the osteoid volume measurement processing of step S35 will be described by referring to FIG. 12. First, the controller 21 acquires the differential phase image data and the absorption image data generated in step S15 (step S91). In the case of the photographing conditions of the example described above, acquired is the differential phase image data whose grating slit direction is the orthogonal direction of the bone load direction. Then, in order to perform calculation with the same physical volume of the differential phase image data and the absorption image data, the controller 21 performs integration processing on the differential phase image of the differential phase image data acquired in step S81 to generate the integration-processed differential phase image data (phase image data) (step S92).

Then, the controller 21 generates difference composite image data acquired by subtracting the absorption image of the absorption image data acquired in step S91 from the phase image of the phase image data generated in step S92 (step S93). Then, the controller 21 sets the measurement target ROI set in step S16 in the trabecular part of the difference composite image of the difference composite image data generated in step S93 (step S94).

Then, the controller 21 calculates an average signal value DTm in the measurement target ROI of the difference composite image set in step S94, sets the calculated average signal value DTm as an osteoid volume indicator Oam (step S95), and ends the osteoid volume measurement processing. The signal integrated value per unit area of the measurement target ROI of the difference composite image may be set instead of the average signal value DTm.

Returning to FIG. 6, the controller 21 executes the cortical width measurement processing (step S38). Here, the cortical width measurement processing of step S38 will be described by referring to FIG. 13. First, the controller 21 acquires one (for example, the grating slit direction is the orthogonal direction of the bone load direction) of the small-angle scattering image data generated in step S15, sets the measurement target ROI set in step S16 in the small-angle scattering image of the acquired small-angle scattering image data, generates a profile of a straight line in the direction crossing the cortical width desired to be measured in the measurement target ROI of the small-angle scattering image, and acquires a cortical width CWd from the generated profile (step S101). The measurement target ROI is set to necessarily include the cortical bone, the cancellous bone, and soft tissue outside the cortical bone.

For example, a straight line L6 of a small-angle scattering image SM3 illustrated in FIG. 21A is designated, and signal values of the straight line corresponding to the distance (pixels) are acquired as the profile of a part of the straight line L6 of the small-angle scattering image SM3 as illustrated in FIG. 21B. Further, the section where the signal intensity of the profile drastically changes is taken as the boundary between the soft tissue and the cortical bone, the boundary between the cortical bone and the cancellous bone tissue, and the distance between both boundaries is taken as the cortical width CWd.

The, the controller 21 acquires a magnification rate M of the photographing conditions inputted in step S11 (step S102). As illustrated in FIG. 2A, the X-ray Talbot photographing device 1 needs to have a distance between the two gratings, so that the subject H is detected as a magnified image. Further, the magnification rate varies depending on photographing systems. Therefore, the magnification rate M is used for correcting the cortical width by a photographing magnification rate condition. While "M=(distance between X-ray focal point and detector)/(distance between X-ray focal point and subject)", "distance between focal point and grating" may be substituted when it is difficult to acquire "distance between focal point and subject" as a denominator.

Then, the controller 21 corrects the cortical width CWd by using the magnification rate M acquired in step S102 to calculate "corrected cortical width CW=CWd/M" (step S103), and ends the cortical width measurement processing.

The cortical width measurement processing may also be configured such that a single piece of differential phase image data or absorption image data is acquired in step S101, and the cortical width CWd is acquired from the differential phase image of the acquired differential phase image data or the absorption image of the acquired absorption image data.

Returning to FIG. 6, the controller 21 executes the cortical porosity measurement processing (step S39). Here, the cortical porosity measurement processing of step S39 will be described by referring to FIG. 14. First, the controller 21 acquires small-angle scattering image data of two directions with grating slit directions different from each other by 90° and absorption image data generated in step S15 (step S111). In the case of the photographing conditions of the example described above, acquired are the two pieces of small-angle scattering image data whose grating slit directions are the parallel direction and the orthogonal direction of the bone load direction and a single piece of the absorption image data.

Then, the controller 21 squares and adds the small-angle scattering image data of two directions acquired in step S111 to generate the composite small-angle scattering image data (step S112). Then, the controller 21 sets the measurement target ROI set in step S16 in the same cortical bone position of the composite small-angle scattering image of the composite small-angle scattering image data generated in step S112 and of the absorption image of the absorption image data acquired in step S111 (step S113).

Then, the controller 21 acquires an average signal intensity Abm of the measurement target ROI of the composite small-angle scattering image and an average signal intensity Ssm of the measurement target ROI of the absorption image (step S114). Further, the controller 21 uses the average signal intensities Abm and Ssm acquired in step S114 to calculate "cortical porosity Copo=Ssm/Abm" (step S115), and ends the cortical porosity measurement processing.

Returning to FIG. 6, the bone characteristic indicator measurement processing is ended. Returning to FIG. 5, when there is small-dividing of the measurement target ROI (YES in step S17), the controller 21 applies the numbers from 1 to i to the small ROIs (assumed to be divided into i-pieces) set in step S16, and substitutes 1 to a variable j (step S19). Then, the controller 21 executes the bone characteristic indicator measurement processing by executing measurement processing while changing the measurement target ROI to the small ROI with the variable j as the measurement processing of the bone characteristic indicators (at least one out of the mineralization degree, the cortical volume, and the cortical porosity) set to be small-divided in step S16, executing the measurement processing similar to step S18 where the measurement target ROI is changed to the small ROI with the variable j as the measurement processing of the bone characteristic indicators (at least one out of the mineralization degree, the cortical volume, and the porosity) set to be small-divided in step S16, and executing the measurement processing similar to step S18 as the measurement processing of other bone characteristic indicators (step S20).

However, in step S20, the measurement processing of the bone characteristic indicators without small-dividing the measurement target ROI is unnecessary and unexecuted for the second time and thereafter.

Then, the controller 21 increments the variable j by 1 (step S21). Then, the controller 21 determines whether or not "variable j=i" (step S22). When it is not "variable j=i" (NO in step S22), the processing is shifted to step S20.

When it is "variable j=i" (YES in step S22), the controller 21 calculates a statistic of the bone characteristic indicators of the small ROIs in the measurement target ROI regarding the bone characteristic indicators set to be small-divided in step S16 out of the bone characteristic indicators measured in step S20 as a bone characteristic indicator statistic (step S24). Examples of the statistic of the bone characteristic indicators may be the average value, the minimum value, the maximum value, the standard deviation, and the node of the signal values of the pixels of each small ROI in the measurement target ROI. The standard deviation, the maximum value, and the minimum value relate to variation of the indicator values in the measurement target ROI, and it is capable of measuring uniformity of the bone strength as well as the partial strength and weakness. Further, the average value, the median, and the node express the tendency of the overall measurement target ROI, and it can be used for overall bone strength measurement.

After step S18 or S23, the controller 21 determines a weight coefficient C1 (1=1 to 9: the number of kinds of the bone characteristic indicators) based on the kinds of the bone characteristic indicators (bone characteristic indicator statistic) acquired in step S18 or S20 and the image conditions input in steps S11, S12, and calculates "bone strength indicator=C1×bone density+C2×trabecular anisotropy+C3×trabecular connectivity+C4×trabecular width+C5×trabecular number+C6×mineralization degree+C7×osteoid volume+C8×cortical width+C9×cortical porosity" by using the bone characteristic indicators (bone characteristic indicator statistic) acquired in step S18 or S25 (step S24). For example, when the bone characteristic indicator statistic of the mineralization degree, the osteoid volume, and the cortical porosity is calculated, calculated is the bone characteristic indicator statistic of "bone strength indicator=C1×bone density+C2×trabecular anisotropy+C3×trabecular connectivity+C4×trabecular width+C5×trabecular number+C6'×bone characteristic indicator statistic of mineralization degree+C7'×bone characteristic indicator statistic of osteoid volume+C8×cortical width+C9'×bone characteristic indicator statistic of cortical porosity".

Then, the controller 21 compares the bone characteristic indicators (bone characteristic indicator statistic) acquired in step S18 or S23 and the bone strength indicator calculated in step S24 with comparison information acquired in step S13, and generates comparison result information thereof (step S25). The comparison result information may be in such a form that a given bone characteristic indicator (bone characteristic indicator statistic) or the bone strength indicator is "x % of standard value (comparison information)" compared to the comparison information as the standard value, for example.

Then, the controller 21 displays the bone characteristic indicators (bone characteristic indicator statistic) acquired in step S18 or S23, the bone strength indicator calculated in step S24, and the comparison result information generated in step S25 on the display unit 23, stores those in the memory 25 (step S26), and ends the bone strength indicator calculation processing.

As described above, the image processing device 2 according to the embodiment calculates the trabecular connectivity, the trabecular width, the trabecular number, the mineralization degree, the osteoid volume, the cortical width, and the cortical porosity as the bone characteristic indicators of the subject from the reconstructed image data generated from the moiré image data acquired by photographing the subject. Therefore, it is possible to easily acquire the bone characteristic indicators as the bone quality factors other than the trabecular anisotropy.

Further, the image processing device 2 calculates the bone density or the bone mineral volume of the subject from the reconstructed image data, and adds the calculated bone characteristic indicators and the calculated bone density or the bone mineral volume by using the weight coefficient to calculate the bone strength indicator of the subject. Therefore, it is possible to calculate and provide highly accurate bone strength indicator by adding the bone characteristic indicators indicating the bone quality.

Further, the image processing device 2 calculates the trabecular anisotropy of the subject from the reconstructed image data, and adds at least one of the calculated bone characteristic indicators, the calculated bone density or the bone mineral volume, and the calculated trabecular anisotropy by using the weight coefficient to calculate the bone strength indicator of the subject. Therefore, it is possible to calculate and provide more accurate bone strength indicator since the trabecular anisotropy is added further to the bone characteristic indicators indicating the bone quality.

Further, the image processing device 2 calculates a ratio between the signal values of the two pieces of small-angle scattering image data whose grating slit directions are set in the parallel direction and the orthogonal direction of the bone load direction of the subject. Therefore, through calculating the trabecular anisotropy only from the trabecular information of the required direction by using human body information, it is possible to reduce the number of times of photographing the subject and the exposure dose.

Further, the image processing device 2 calculates the trabecular connectivity by using the differential phase image data. Therefore, the use of the differential phase image makes it possible to detect thin trabecula that cannot be detected with the conventional absorption image, so that more accurate trabecular connectivity can be acquired.

Furthermore, the image processing device 2 calculates the trabecular number based on the pixel number exceeding a prescribed threshold value in the profile of the differential phase image data. Therefore, the use of the differential phase image makes it possible to detect thin trabecula that cannot be detected with the conventional absorption image, so that more accurate trabecular number can be acquired.

Further, the image processing device 2 performs a frequency analysis of the profile of the differential phase image data, and calculates the length corresponding to the spatial frequency of the highest spectrum intensity within the spatial frequency corresponding to the trabecula as the trabecular width. Therefore, the use of the differential phase image makes it possible to detect thin trabecula that cannot be detected with the conventional absorption image, and the trabecular width of fine accuracy can be acquired by eliminating the influence of artifact by the frequency analysis.

Further, the image processing device 2 uses the composite differential phase image data acquired by squaring and adding the two pieces of differential phase image data (integrated differential phase image data) whose grating slit directions with respect to the subject are different from each other by 90° to calculate the trabecular connectivity (preferably the trabecular number and the trabecular width as well). Therefore, since information in the orthogonal direction of the grating cannot be acquired with the differential phase image of one-dimensional grating, the use of the composite image of the two differential phase images of different angles makes it possible to acquire more accurate trabecular connectivity (as well as the trabecular number and the trabecular width).

Further, the image processing device 2 calculates the average signal value of the small-angle scattering image data as the mineralization degree. Therefore, the mineralization degree can be acquired with less invasiveness on living bodies.

Further, the image processing device 2 may calculate the mineralization degree by using the composite small-angle scattering image data acquired by squaring and adding the two pieces of small-angle scattering image data whose grating slit directions with respect to the subject are different from each other by 90°. Therefore, the use of the composite image of the two small-angle scattering images of different angles makes it possible to acquire more accurate mineralization degree with less invasiveness on living bodies. With the configuration where the image processing device 2 calculates the average signal value of the small-angle scattering image data as the mineralization degree, the mineralization degree can be acquired with less invasiveness on living bodies.

Further, the image processing device 2 performs correction by multiplying the correction coefficient calculated by using the absorption image data on the mineralization degree acquired from the small-angle scattering image data. Therefore, more accurate mineralization degree can be acquired with less invasiveness on living bodies.

Further, when the bone characteristic indicator to be calculated is at least one of the mineralization degree, the osteoid volume, and the cortical porosity, the image processing device 2 calculates the bone characteristic indicator for each of a plurality of small ROIs acquired by dividing the measurement target ROI of the reconstruction image data, and calculates the statistic of the plurality of calculated bone characteristic indicators. Therefore, the statistic of the bone characteristic indicators such as in-plane variation of the mineralization progress degree can be acquired easily.

Further, the image processing device 2 calculates, as the osteoid volume, the signal integration value or the average value of the signal values in the trabecular region of the different image data between the phase image data acquired by performing integration processing on the differential phase image data and the absorption image data. Therefore, the osteoid volume can be acquired with less invasiveness on living bodies.

Further, the image processing device 2 acquires the cortical width from the profile of the reconstruction image data including the cortical bone and the cancellous bone. Therefore, the cortical width can be acquired with fine accuracy. Especially, by using the small-angle scattering image data as the reconstruction image data, the boundaries between the cortical bone and other substances can be observed more clearly than the case of the absorption image. Therefore, the cortical width can be acquired more accurately than the case of using existing devices.

Further, the image processing device 2 corrects the cortical width by using the magnification rate M based on the photographing conditions of the subject. Therefore, it is possible to acquire more accurate cortical width by performing correction calculation of deviation in the bone characteristic indicator values by the photographing conditions.

Further, the image processing device 2 acquires the average signal intensities of the measurement targets ROI at the same positions of the inside of the cortical bones of the small-angle scattering image data and the absorption image data, and calculates the ratio between the two acquired average signal intensities as the cortical porosity. Therefore, the cortical porosity can be acquired with less invasiveness on living bodies.

Further, the X-ray photographing system 100 includes: the X-ray Talbot photographing device 1 that photographs a subject and generates moiré image data; and the image processing device 2 that generates reconstructed image data from the moiré image data and calculates the bone characteristic indicators (the trabecular connectivity, the trabecular width, the trabecular number, the mineralization degree, the osteoid volume, the cortical width, and the cortical porosity) (the bone density or the bone mineral volume, the trabecular anisotropy, the bone strength indicator) from the reconstructed image data. Therefore, the bone characteristic indicators as the bone quality factors other than the trabecular anisotropy can be acquired easily by photographing the subject.

Note that the descriptions of the embodiments above are illustrative examples of a preferable medical image processing device and medical image photographing system according to the present disclosure, and not intended to be limited thereto.

For example, while the embodiment described above employs the configuration where the bone strength indicator is calculated by using the bone characteristic indicators of the whole kinds (the bone characteristic indicator statistic), calculation thereof is not limited to that. It is also possible to employ a configuration in which the bone strength indicator is calculated by using the bone density or the bone mineral volume and at least one of the bone characteristic indicators (bone characteristic indicator statistic) such as the trabecular anisotropy, the trabecular connectivity, the trabecular width, the trabecular number, the mineralization degree, the osteoid volume, the cortical width, and the cortical porosity. Which of the bone characteristic indicators is to be used is selected and inputted by the operator, for example.

Further, while the embodiment described above employs the configuration where at least one of the mineralization degree, the osteoid volume, and the cortical porosity is selected, and the bone characteristic indicator statistic is calculated while dividing the measurement target ROI into the small ROIs, calculation thereof is not limited to that. When the measurement target ROI is divided into the small ROIs, the mineralization degree, the osteoid volume, and the cortical porosity are highly effective as the statistic of the bone characteristic indicators. It is also possible to employ a configuration where the measurement target ROI is divided into small ROIs also for the bone characteristic indicators other than the mineralization degree, the osteoid volume, and the cortical porosity and the statistic of the bone characteristic indicators is calculated.

Further, it is also possible to employ a configuration where the measurement target ROI is divided into small ROIs to calculate the bone strength indicators of each of the small ROIs, and the statistic of the bone strength indicators is calculated as the bone strength indicator statistic. With such configuration, the statistic of the bone strength indicators indicating variation and the like of the bone strength indicators can be acquired easily.

Further, while the embodiment described above employs the configuration where the image processing device 2 uses the magnification rate M to correct the cortical width based on the photographing conditions of the subject, correction thereof is not limited to that. For example, it is also possible to employ a configuration where the image processing device 2 corrects the cortical width or the bone characteristic indicators other than the cortical width based on at least either the photographing body parts or the photographing conditions of the subject. With such configuration, more accurate bone characteristic indicators can be acquired by performing correction calculation of the deviation in the bone characteristic indicator values caused by a difference in the bone structures depending on the photographing body parts of the subject and the photographing conditions.

Further, it is also possible to employ a configuration where the image processing device 2 corrects the bone strength indicator based on at least either the photographing body parts or the photographing conditions of the subject. With such configuration, more accurate bone strength indicator can be acquired by performing correction calculation of the deviation in the bone characteristic indicator values caused by a difference in the bone structures depending on the photographing body parts of the subject and the photographing conditions.

Further, while the embodiment described above employs the configuration where the subject is photographed such that the angles of the grating slit direction with respect to the subject of the reconstructed image data become the parallel direction and the orthogonal direction of the bone load direction, photographing of the subject is not limited to that. For example, when the subject is photographed with the angles of the grating slit direction with respect to the subject being shifted from the parallel direction and the orthogonal direction of the bone load direction, it is also possible to employ a configuration where the controller 21 of the image processing device 2 corrects the signal values or the bone characteristic indicators of the reconstructed image data so that those angles are corrected to the angles with respect to the bone load direction of the subject. With such configuration, the necessary number of photographed pieces and the exposure dose of the subject can be reduced by correcting the signal values of the reconstructed image data or the bone characteristic indicators based on the angles of the grating slit direction with respect to the subject.

Further, detailed configurations and operations of each component of the X-ray photographing system 100 according to the above-described embodiment can be changed as appropriate without departing from the spirit and scope of the present disclosure. Although embodiments of the present disclosure have been described and illustrated in detail, the disclosed embodiments are made for purposes of illustration and example only and not limitation. The scope of the present disclosure should be interpreted by terms of the appended claims.

As used herein, the words "can" and "may" are used in a permissive (i.e., meaning having the potential to), rather than mandatory sense (i.e., meaning must). The words "include," "includes," "including," and the like mean including, but not limited to. Similarly, the singular form of "a" and "the" include plural references unless the context clearly dictates otherwise. And the term "number" shall mean one or an integer greater than one (i.e., a plurality).

What is claimed is:

1. A medical image processing device, comprising:
    a hardware processor that (i) calculates at least one of trabecular connectivity, trabecular width, trabecular number, mineralization degree, osteoid volume, cortical width, and cortical porosity as a bone characteristic indicator of a subject from reconstructed image data generated from moiré image data acquired by photographing the subject, (ii) evaluates a risk of the subject's bone having a fracture based on the at least one calculation, (iii) calculates bone density or bone mineral volume of the subject from the reconstructed image data, and (iv) calculates a bone strength indicator based on an addition involving the calculated bone characteristic indicator, the calculated bone density or bone mineral volume, and a weight coefficient; and
    a display that displays at least one of the bone characteristic indicator and the bone strength indicator.

2. The medical image processing device according to claim 1, wherein the hardware processor corrects the bone characteristic indicator based on at least one of a photographed body part of the subject and a photographing condition.

3. The medical image processing device according to claim 1, wherein the hardware processor corrects the bone strength indicator based on at least one of a photographed body part of the subject and a photographing condition.

4. The medical image processing device according to claim 1, wherein the hardware processor calculates the bone strength indicator for each of a plurality of small regions acquired by dividing a measurement target region of the reconstructed image data, and calculates a statistic of a plurality of calculated bone strength indicators.

5. The medical image processing device according to claim 1, wherein the hardware processor calculates trabecular anisotropy of the subject from the reconstructed image data, and adds at least one of the calculated bone characteristic indicators, the calculated bone density or bone mineral volume, and the calculated trabecular anisotropy by using a weight coefficient to calculate the bone strength indicator of the subject.

6. The medical image processing device according to claim 5, wherein the hardware processor calculates, as the trabecular anisotropy, a ratio between signal values of two pieces of small-angle scattering image data as the reconstructed image data in which a grating slit direction is set as a parallel direction and an orthogonal direction of a bone load direction of the subject.

7. The medical image processing device according to claim 1, wherein the hardware processor corrects a signal value of the reconstructed image data or the bone characteristic indicator such that an angle of a grating slit direction with respect to the subject when photographing the moiré image data comes to an angle with respect to a bone load direction of the subject.

8. The medical image processing device according to claim 1, wherein the hardware processor calculates the trabecular connectivity by using differential phase image data as the reconstructed image data.

9. The medical image processing device according to claim 1, wherein the hardware processor calculates the trabecular number based on pixel number exceeding a prescribed threshold value on a profile of differential phase image data as the reconstructed image data.

10. The medical image processing device according to claim 1, wherein the hardware processor performs a frequency analysis of a profile of differential phase image data as the reconstructed image data and calculates, as the trabecular width, a length corresponding to a spatial frequency of the highest spectrum intensity within the spatial frequency corresponding to a trabecula.

11. The medical image processing device according to claim 1, wherein the hardware processor calculates at least one of the trabecular connectivity, the trabecular number, and the trabecular width by using composite differential phase image data acquired by squaring and adding two pieces of differential phase image data as the reconstructed image data whose angles of grating slit directions with respect to the subject are different from each other by 90°.

12. The medical image processing device according to claim 1, wherein the hardware processor calculates the mineralization degree by using composite small-angle scattering image data acquired by squaring and adding two pieces of small-angle scattering image data as the reconstructed image data whose angles of grating slit directions with respect to the subject are different from each other by 90°.

13. The medical image processing device according to claim 1, wherein the hardware processor calculates, as the mineralization degree, an average signal value of small-angle scattering image data as the reconstructed image data.

14. The medical image processing device according to claim 12, wherein the hardware processor performs correction by multiplying a correction coefficient that is calculated by using absorption image data as the reconstructed image data on the mineralization degree acquired from the small-angle scattering image data.

15. The medical image processing device according to claim 1, wherein the hardware processor calculates the bone characteristic indicator for each of a plurality of small regions acquired by dividing a measurement target region of the reconstructed image data, and calculates a statistic of a plurality of calculated bone characteristic indicators.

16. The medical image processing device according to claim 1, wherein the hardware processor calculates, as the osteoid volume, a signal integrated value or an average value of signal values in a trabecular region of a difference image data between a phase image data acquired by performing integration processing on differential phase image data as the reconstructed image data and absorption image data as the reconstructed image data.

17. The medical image processing device according to claim 1, wherein the hardware processor acquires the cortical width from a profile including a cortical bone and a cancellous bone of the reconstructed image data.

18. The medical image processing device according to claim 1, wherein the hardware processor acquires average signal intensities of measurement target regions at same positions inside cortical bones of small-angle scattering image data as the reconstructed image data and of absorption image data, and calculates a ratio between the two acquired average signal intensities as the cortical porosity.

19. A medical image photographing system, comprising:
the medical image processing device according to claim 1; and
a medical image photographing device that photographs the subject and generates the moiré image data, wherein
the hardware processor generates reconstructed image data from the moiré image data.

* * * * *